United States Patent
Liu et al.

(10) Patent No.: US 11,187,669 B2
(45) Date of Patent: *Nov. 30, 2021

(54) FIELD MEASUREMENT OF SOIL ELEMENT CONCENTRATION

(71) Applicant: THE CLIMATE CORPORATION, San Francisco, CA (US)

(72) Inventors: Miao Liu, Grover, MO (US); Luis Jurado, St. Louis, MO (US)

(73) Assignee: The Climate Corporation, San Francisco, CA (US)

(*) Notice: Subject to any disclaimer, the term of this patent is extended or adjusted under 35 U.S.C. 154(b) by 155 days.

This patent is subject to a terminal disclaimer.

(21) Appl. No.: 16/696,770

(22) Filed: Nov. 26, 2019

(65) Prior Publication Data

US 2020/0173954 A1 Jun. 4, 2020

Related U.S. Application Data

(63) Continuation of application No. 15/723,177, filed on Oct. 3, 2017, now Pat. No. 10,488,363.

(51) Int. Cl.
*G01N 33/24* (2006.01)
*G01N 1/08* (2006.01)
(Continued)

(52) U.S. Cl.
CPC .............. *G01N 27/333* (2013.01); *G01N 1/04* (2013.01); *G01N 1/08* (2013.01); *G01N 1/4044* (2013.01);
(Continued)

(58) Field of Classification Search
CPC ........... H04L 67/12; H04L 67/18; G01N 1/04; G01N 1/08; G01N 1/4044;
(Continued)

(56) References Cited

U.S. PATENT DOCUMENTS 5,384,247 A 1/1995 Berry et al.
6,484,652 B1 11/2002 Colburn, Jr.
(Continued)

FOREIGN PATENT DOCUMENTS

WO  WO 98/53312 A1  11/1998

OTHER PUBLICATIONS

Liu, U.S. Appl. No. 15/723,177, filed Oct. 30, 2017, Notice of Allowance, dated Aug. 30, 2019.
(Continued)

*Primary Examiner* — Jennifer Wecker
(74) *Attorney, Agent, or Firm* — Hickman Becker Bingham Ledesma LLP

(57) ABSTRACT

In an embodiment, a system for measuring soil element concentration in a field in real time is disclosed. The system comprises an extraction apparatus coupled to a mobility component configured to move the system in the agricultural field. The extraction apparatus configured to receive a plurality of soil samples successively from a soil probe coupled to the mobility component, when the mobility component is operating. The extraction apparatus containing an extractant solution that is a solvent of the soil samples. In addition, the extraction apparatus comprising a mixer that is configured to mix the soil samples with the extractant solution, thereby forming a solution mix. The system also comprises a chemical sensor coupled to the extraction apparatus, the chemical sensor configured to measure a concentration level of a soil element in the solution mix. Furthermore, the system comprises a processor coupled to the chemical sensor, the processor configured to calculate a concentration level of the soil element in each of the plurality of soil samples after the
(Continued)

soil sample is received by the extraction apparatus and before a successive soil sample is received by the extraction apparatus.

20 Claims, 10 Drawing Sheets

(51) Int. Cl.
| | |
|---|---|
| *G01N 1/04* | (2006.01) |
| *G01N 1/02* | (2006.01) |
| *G01N 1/28* | (2006.01) |
| *G01N 27/333* | (2006.01) |
| *H04L 29/08* | (2006.01) |
| *G01N 1/40* | (2006.01) |
| *G01N 21/25* | (2006.01) |

(52) U.S. Cl.
CPC ............. *G01N 33/24* (2013.01); *H04L 67/12* (2013.01); *G01N 21/25* (2013.01); *G01N 2001/021* (2013.01); *G01N 2001/2866* (2013.01); *G01N 2001/4061* (2013.01); *G01N 2001/4088* (2013.01); *G01N 2033/245* (2013.01); *H04L 67/18* (2013.01)

(58) Field of Classification Search
CPC ..... G01N 2001/021; G01N 2001/2866; G01N 2001/4061; G01N 2001/4088; G01N 2033/245; G01N 21/25; G01N 27/333; G01N 33/24; A01C 21/007; A01B 79/005
See application file for complete search history.

(56) References Cited

U.S. PATENT DOCUMENTS

| | | |
|---|---|---|
| 2005/0172733 A1 | 8/2005 | Drummond et al. |
| 2012/0161790 A1 | 6/2012 | Smith |
| 2013/0247655 A1* | 9/2013 | Preiner .................. G01N 33/24 73/61.59 |
| 2014/0012504 A1 | 1/2014 | Ben-Dor |
| 2017/0169523 A1 | 6/2017 | Xu et al. |
| 2019/0101505 A1 | 4/2019 | Liu |

OTHER PUBLICATIONS

Liu, U.S. Appl. No. 15/723,177, filed Oct. 3, 2017, Office Action, dated Jun. 14, 2019.
Liu, U.S. Appl. No. 15/723,177, filed Oct. 3, 2017, Corrected Notice of Allowability, dated Oct. 9, 2019.
International Searching Authority, "Search Report", In application No. PCT/US2018/054007, dated Dec. 11, 2018, 16 pages.
Current Claims in Application No. PCT/US2018/054007, Dec. 2018, 4 pages.
Current Claims in application No. 2018800771015, dated Jun. 21, 2021, 3 pages.
Current Claims in application No. 2018800771015, dated Jan. 5, 2021, 3 pages.
China Patent Office, "Office Action" in application No. 2018800771015 dated Jun. 21, 2021, 4 pages.
China Patent Office, "Office Action" in application No. 2018800771015 dated Jan. 5, 2021, 4 pages.

* cited by examiner

Fig. 2
(a)
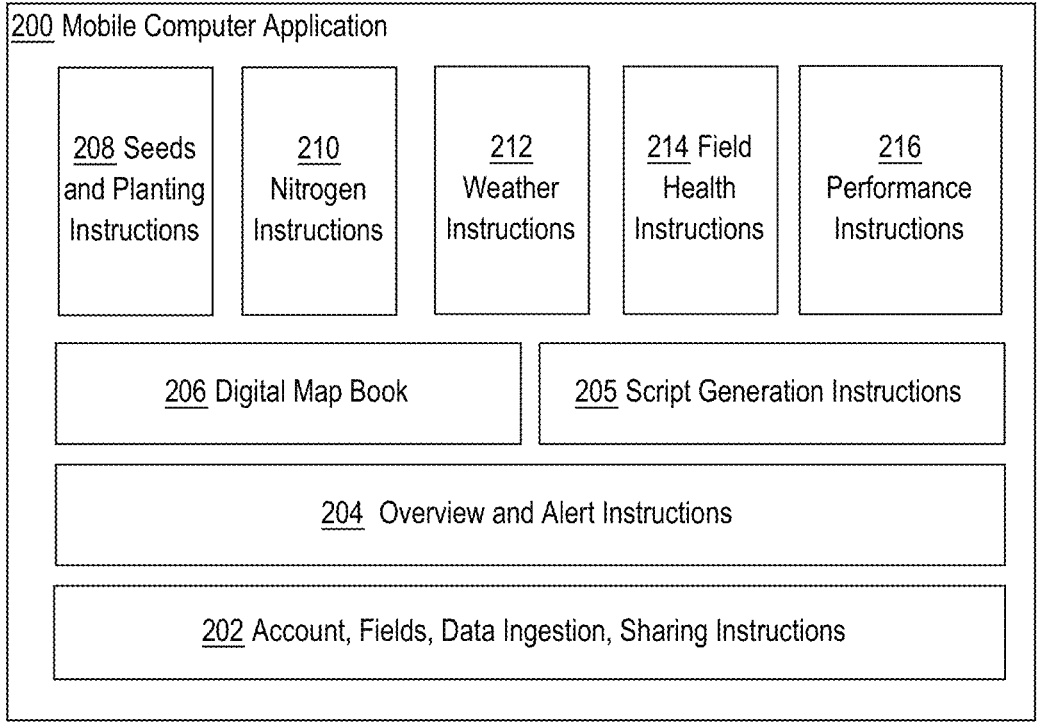
(b)
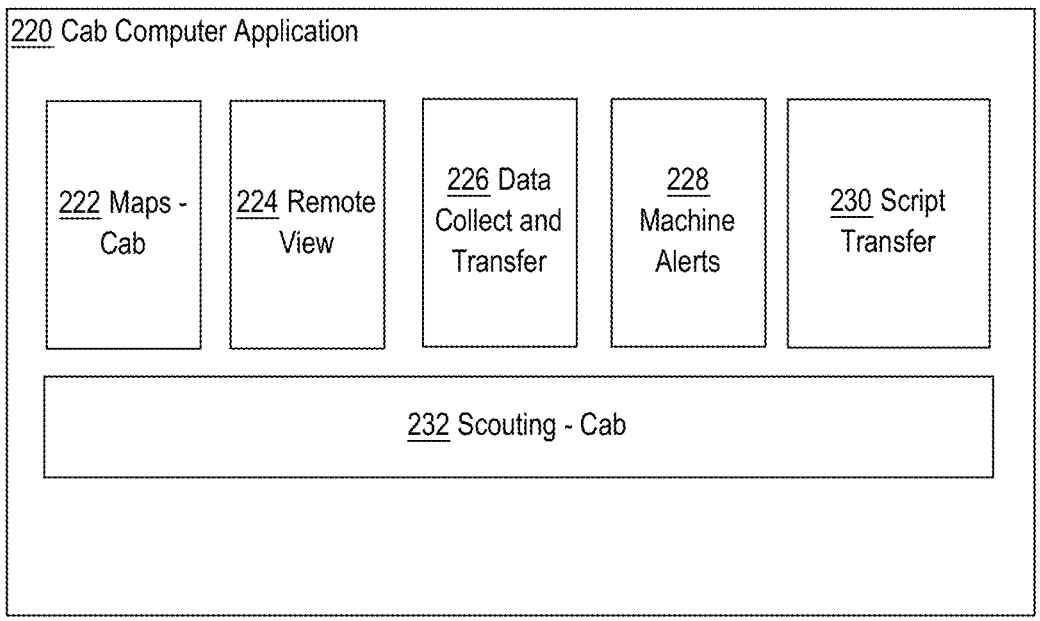

FIG. 5

Data Manager

[Nitrogen] [Planting] [Practices] [Soil]

Planting 1 (4 Fields)
Crop Corn Product
Plant Date: 2016-04-12
ILU 112 | Pop: 34000
[Edit] [Apply]

Planting 2 (0 Fields)
Crop Corn Product
Plant Date: 2016-04-15
ILU 83 | Pop: 34000
[Edit] [Apply]

Planting 3 (0 Fields)
Crop Corn Product
Plant Date: 2016-04-13
ILU 83 | Pop: 34000
[Edit] [Apply]

Planting 4 (1 Fields)
Crop Corn Product
Plant Date: 2016-04-13
ILU 112 | Pop: 34000
[Edit] [Apply]

Add New Planting Plan +

| | CROP | PLANTED ACRES | PRODUCT | RELATIVE MATURITY | TARGET YIELD | POPULATION (AVG) | PLA |
|---|---|---|---|---|---|---|---|
| ☐ Select All | | | | | | | |
| ☐ Ames, IA 1<br>Corn \| 100 \| Boone, IA | Corn | — | DMC82-M | 112 | 160 | 34000 | Apr |
| ☐ Austin, MN 1<br>Corn \| 100 \| Fredricks, MN | Corn | — | DMC82-M | 114 | 160 | 36000 | Apr |
| ☐ Boone, IN 1<br>Corn \| 100 \| Boone, IA | Corn | — | DMC82-M | 112 | 150 | 34000 | Apr |
| ☐ Champaign 1<br>Corn \| 100 \| Champaign, IL | Corn | — | — | 112 | 200 | 34000 | Apr |
| ☐ E Nebraska 1<br>Corn \| 100 \| Burt, NE | Corn | — | — | 112 | 160 | 34000 | Apr |

*FIG. 6*

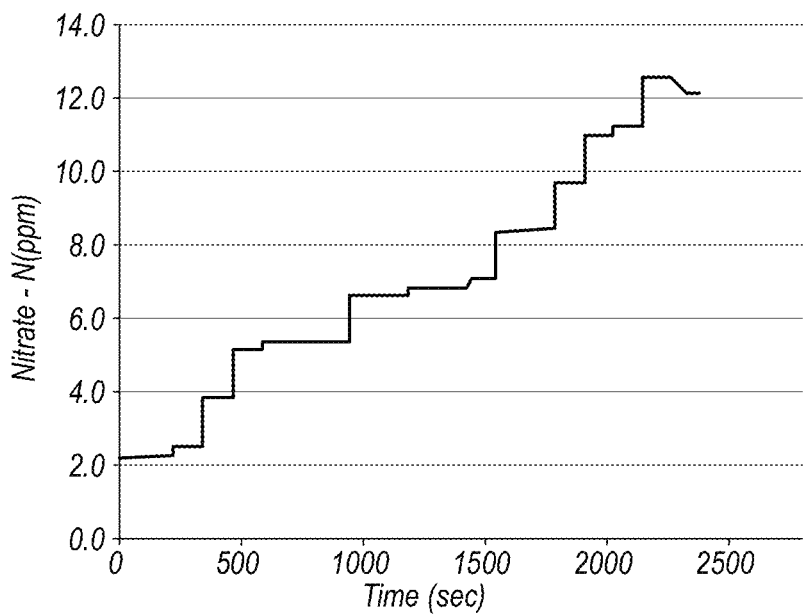
FIG. 10A
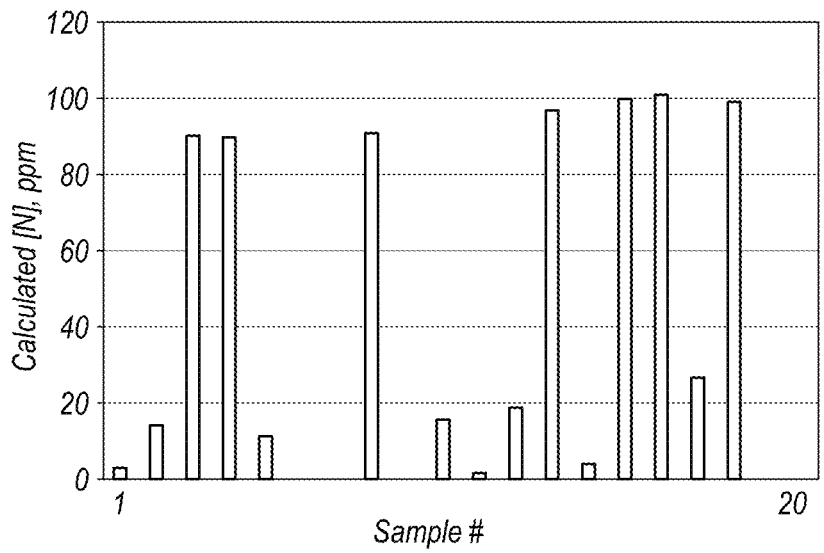
FIG. 10B
| N | 20 |
|---|---|
| Soil [NO3-] - Lab Measured | 102 |
| Avg [NO3-] - Cartridge Measured | 97 |
| Std Dev | 6.9 |
| % Recovery | 95 |
| Precision (% CV) | 7.1 |
| Accuracy (% Relative Error) | -5.3 |
FIG. 10C

FIELD MEASUREMENT OF SOIL ELEMENT CONCENTRATION

BENEFIT CLAIM

This application claims the benefit under 35 U.S.C. § 120 as a Continuation of application Ser. No. 15/723,177, filed Oct. 3, 2017, the entire contents of which are hereby incorporated by reference for all purposes as if fully set forth herein. Applicant hereby rescinds any disclaimer of claim scope in the parent applications or the prosecution history thereof and advises the USPTO that the claims in this application may be broader than any claim in the parent applications.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright or rights whatsoever. © 2015-2019 The Climate Corporation.

FIELD OF THE DISCLOSURE

The present disclosure relates to soil content measurement and particularly to real-time measurement of soil element concentration in a field.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

A grower benefits from healthy soil. Maintaining healthy soil often includes accurately tracking the amounts of nutrients, such as nitrate, in the soil. The amount of nitrate or another type of nutrient in soil can vary with the location within a field, sampling time, environmental conditions, or soil physical characteristics, with soil type, moisture, and temperature having a significant effect in particular.

One common approach for measuring the concentration level of a particular soil element involves collecting a sample of soil from a field, sending the soil sample to a laboratory, and receiving a measurement of the concentration level from the laboratory after a few days or even weeks. However, the concentration level can change quickly over time due to the various factors noted above. For example, the amount of nitrate is expected to decrease by several folds during shipping from the field to the laboratory. Thus, the measurement obtained from the laboratory may not accurately reflect the concentration level of the particular soil element at the time when the soil sample was taken.

SUMMARY

The appended claims may serve as a summary of the disclosure.

BRIEF DESCRIPTION OF THE DRAWINGS

In the drawings:

FIG. 2 illustrates two views of an example logical organization of sets of instructions in main memory when an example mobile application is loaded for execution.

FIG. 5 depicts an example embodiment of a timeline view for data entry.

FIG. 6 depicts an example embodiment of a spreadsheet view for data entry.

FIG. 10A illustrates an example diagram showing how the nitrate concentration level in the solution mix changed as a certain number of soil samples were successively mixed into the extractant solution, as measured by the chemical sensor.

FIG. 10B illustrates an example diagram showing the nitrate concentration level in each of the certain number of soil samples successively added to the solution mix, as computed by the processor.

FIG. 10C illustrates sample statistics related to the experiment.

DETAILED DESCRIPTION

Figure 1:
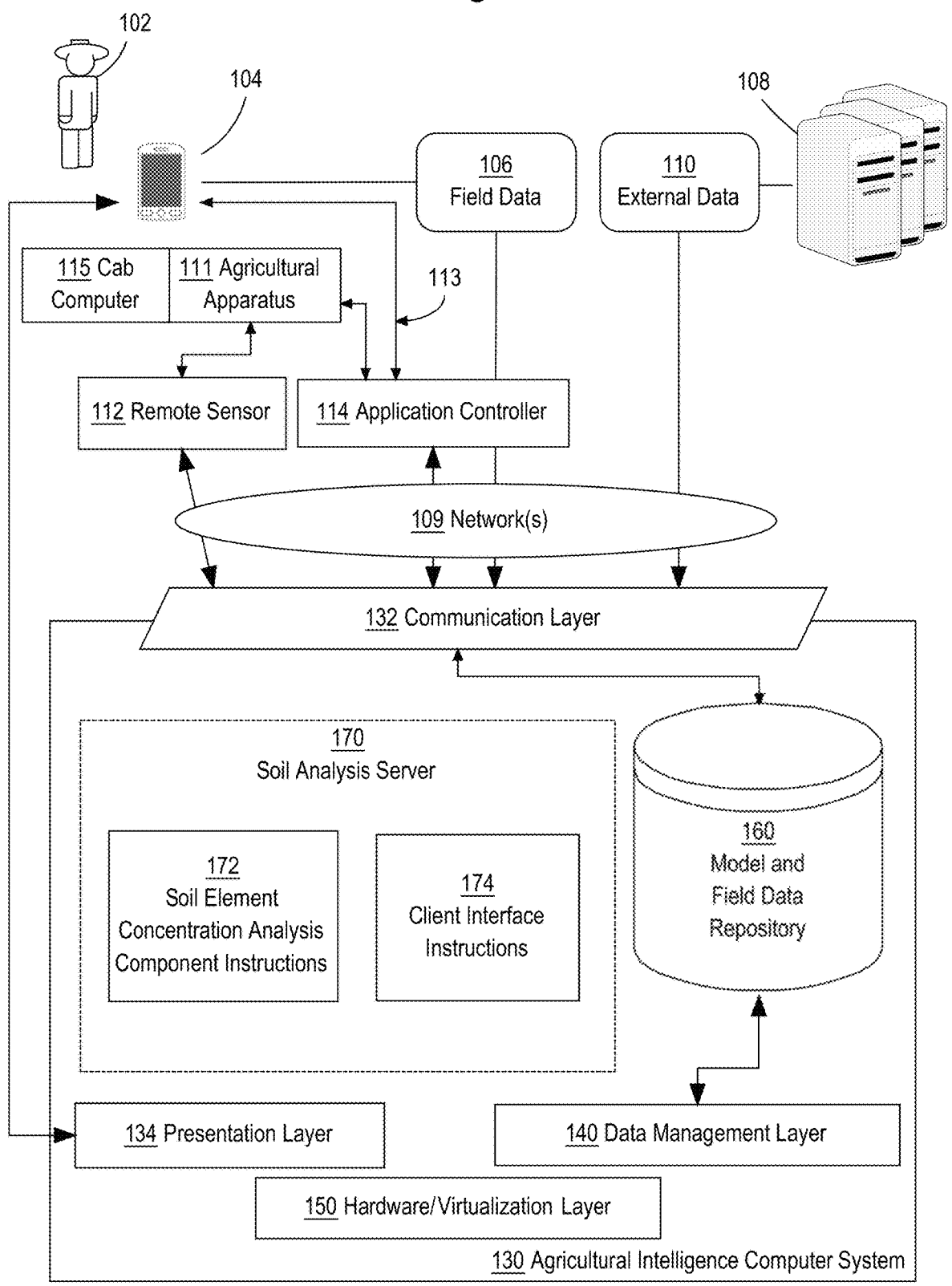
FIG. 1 illustrates an example computer system that is configured to perform the functions described herein, shown in a field environment with other apparatus with which the system may interoperate.

In the following description, for the purposes of explanation, numerous specific details are set forth in order to provide a thorough understanding of the present disclosure. It will be apparent, however, that embodiments may be practiced without these specific details. In other instances, well-known structures and devices are shown in block diagram form in order to avoid unnecessarily obscuring the present disclosure. Embodiments are disclosed in sections according to the following outline:

1. GENERAL OVERVIEW
2. EXAMPLE AGRICULTURAL INTELLIGENCE COMPUTER SYSTEM
  2.1. STRUCTURAL OVERVIEW
  2.2. APPLICATION PROGRAM OVERVIEW
  2.3. DATA INGEST TO THE COMPUTER SYSTEM
  2.4 PROCESS OVERVIEW—AGRONOMIC MODEL TRAINING
  2.5 SOIL ANALYSIS
  2.6 IMPLEMENTATION EXAMPLE—HARDWARE OVERVIEW

3. MOBILE SOIL ANALYSIS SYSTEM
3.1 SYSTEM OVERVIEW
3.2 REAL-TIME SOIL EXTRACTION, SENSING, AND MEASUREMENT UNIT

1. General Overview

A mobile soil analysis system for measuring soil element concentration in a field in real time is disclosed. Applications of the system include fall soil nutrient analysis as well as soil chemical analysis at the time of planting (early or late spring) and during the growing season. In an embodiment, the system includes an apparatus that can receive successive soil samples and measure the concentration level of a target soil element, such as nitrate or nitrogen, in each of the soil samples in real time. The apparatus can comprise a cartridge for holding an extractant solution, an automated mixer for mixing soil samples into the extractant solution, a selective chemical sensor for measuring the concentration level of the target soil element in the mix, and a processor for calculating the concentration level of the target soil element in each soil sample from sensor data. The system can further include a mobility component that allows the system to be applied across a field, a soil probe for collecting successive soil samples as the system travels, and a location sensor for tracking soil collection locations or other location data. The system can complete the process from collecting a soil sample to determining a concentration level of the target soil element within a matter of seconds and can immediately repeat this process. Given location data, expected yield levels, or other additional data, the processor can be further configured to produce recommendations on adjusting the concentration levels of the soil target element in real time.

In an embodiment, a real-time on-the-go ("OTG") analytical method for directly measuring nitrate (nitrogen) in soils is disclosed, composed of a cartridge-like apparatus containing an extracting solution, an automated mixer, and a selective sensor for measuring the target chemicals nutrients (i.e., nitrate/nitrogen) in a sequential way across the field. A data system for capturing the GPS coordinates as well as the measured nitrate from where the sample(s) was taken is linked to automated calculator software which together with entering the detected amounts of nitrate/nitrogen and the GPS coordinates from where the sample was taken will allow triggering the specific application of fertilizer needed for growing a specific crop. In an embodiment, such an OTG apparatus and method permits rapidly estimating the amount of soil nitrate (nitrogen) while moving across the field. The output data can be used to then customize the site-specific fertilizer/nitrate (nitrogen) application plans for the farmer's crop of interest. The entire system includes a moving vehicle to carry and transport the whole apparatus across the field, an automated soil probe for collecting a target sample from the field at a defined soil depth, a cartridge-like device with a specified volume of extractant solution(s), a selective chemical sensor for nitrate, nitrogen or other compounds or elements and for rapidly measuring the specific soil chemical nutrient, a GPS system for capturing the location to where the sample is taken, and a computer with control software for controlling sample collection, target analyte measured, storing the data, and calculating the amount of fertilizer application for the field being analyzed.

In an embodiment, for on-the-go measurements of soil nitrate as they are collected, a removable cartridge-like device is in a moving vehicle. In an embodiment, the cartridge-like device has openings for introducing a specified volume of target soil sample, to introduce the sensor and for having an automated mixer. In addition, the cartridge-like device may contain a specified volume of an extractant solution capable of rapidly mixing the soil and dissolving the target analyte once it is introduced and measured with the selective nitrate/nitrogen sensor. With the goal of analyzing several soil samples, the cartridge will be built of a specified size (e.g., gallons capacity) capable of holding the addition of sequential number of soil samples within the same volume of extractant solution. This cartridge-like device can be mounted in a vehicle when moving across the field. In addition, the above system will be coupled to a computer and software system for operating the method, collecting the measured data and for capturing the GPS coordinates to where each of the sample(s) were taken. Such a system will provide as output the nutrient amounts present in that field area where the sample was taken and the output may trigger an alarm signaling the simultaneous addition or not of a specified amount of fertilizer for compensating for nutrient target amounts needed for growing a specific crop with a defined target yield.

In an embodiment, a soil measurement system comprises a moving vehicle to load and transport the cartridge-like device across the field, a soil probe(s) for collecting a target sample from the field at a defined soil depth, a cartridge-like device with a specified volume of extractant solution(s), a selective chemical sensor for rapidly measuring specific soil chemical components (e.g., nitrate/nitrogen sensor), a GPS for capturing the location to where the sample is taken, and a computer with a custom-made software for controlling the whole operation—sample collection, target analyte measuring and storing the data.

In some embodiments, a mobile soil analysis system enables growers to precisely and intensely analyze soil nutrient variations under numerous field conditions. Specifically, the system can assist a grower in real-time management of fertilizing decisions to achieve expected crop yield response. For example, the system can help a grower determine an appropriate time, amount, or place (i.e., field zone area) for applying or not applying fertilizers or for selecting a specific crop seed hybrid/variety that may produce an optimal yield under the farmer's field conditions and nutrient measurements. By providing real-time measurements of soil element concentration, the system can also facilitate research development of new crop varieties with enhanced fertilizer use properties. In addition, the system can assist a user in real-time monitoring of fields with a high vulnerability for chemical pollution to handle soil nutrient loss, thus contributing to current sustainability environmental practices.

Embodiments provide the benefits of helping farmers sustainably increase productivity by applying fertilizers at the right place with right amounts. Embodiments may provide the benefit of permitting verifying that the current fertilization program will supply adequate nitrate fertility to the current year's crop and to determine how much supplemental nitrogen is needed. Furthermore, since some fields do not respond to nitrogen, having an OTG testing will be one way to screen out those fields. An OTG system may allow measuring fields after wet seasons and/or to determine nitrate carryover after a drought. Checking fields that have different crop rotations and history of manure applications will be possible with embodiments as well.

Embodiments may provide the specific benefit of an on-the-go nitrate measurement system for accurately and precisely quantifying heterogeneous soils with nitrate levels from 5-25 ppm, a field resolution of a sample every 10 feet, and a sampling depth of 6-12 inches.

2. Example Agricultural Intelligence Computer System

2.1 Structural Overview

FIG. 1 illustrates an example computer system that is configured to perform the functions described herein, shown in a field environment with other apparatus with which the system may interoperate. In one embodiment, a user 102 owns, operates or possesses a field manager computing device 104 in a field location or associated with a field location such as a field intended for agricultural activities or a management location for one or more agricultural fields. The field manager computer device 104 is programmed or configured to provide field data 106 to an agricultural intelligence computer system 130 via one or more networks 109.

Examples of field data 106 include (a) identification data (for example, acreage, field name, field identifiers, geographic identifiers, boundary identifiers, crop identifiers, and any other suitable data that may be used to identify farm land, such as a common land unit (CLU), lot and block number, a parcel number, geographic coordinates and boundaries, Farm Serial Number (FSN), farm number, tract number, field number, section, township, and/or range), (b) harvest data (for example, crop type, crop variety, crop rotation, whether the crop is grown organically, harvest date, Actual Production History (APH), expected yield, yield, crop price, crop revenue, grain moisture, tillage practice, and previous growing season information), (c) soil data (for example, type, composition, pH, organic matter (OM), cation exchange capacity (CEC)), (d) planting data (for example, planting date, seed(s) type, relative maturity (RM) of planted seed(s), seed population), (e) fertilizer data (for example, nutrient type (Nitrogen, Phosphorous, Potassium), application type, application date, amount, source, method), (f) chemical application data (for example, pesticide, herbicide, fungicide, other substance or mixture of substances intended for use as a plant regulator, defoliant, or desiccant, application date, amount, source, method), (g) irrigation data (for example, application date, amount, source, method), (h) weather data (for example, precipitation, rainfall rate, predicted rainfall, water runoff rate region, temperature, wind, forecast, pressure, visibility, clouds, heat index, dew point, humidity, snow depth, air quality, sunrise, sunset), (i) imagery data (for example, imagery and light spectrum information from an agricultural apparatus sensor, camera, computer, smartphone, tablet, unmanned aerial vehicle, planes or satellite), (j) scouting observations (photos, videos, free form notes, voice recordings, voice transcriptions, weather conditions (temperature, precipitation (current and over time), soil moisture, crop growth stage, wind velocity, relative humidity, dew point, black layer)), and (k) soil, seed, crop phenology, pest and disease reporting, and predictions sources and databases.

A data server computer 108 is communicatively coupled to agricultural intelligence computer system 130 and is programmed or configured to send external data 110 to agricultural intelligence computer system 130 via the network(s) 109. The external data server computer 108 may be owned or operated by the same legal person or entity as the agricultural intelligence computer system 130, or by a different person or entity such as a government agency, non-governmental organization (NGO), and/or a private data service provider. Examples of external data include weather data, imagery data, soil data, or statistical data relating to crop yields, among others. External data 110 may consist of the same type of information as field data 106. In some embodiments, the external data 110 is provided by an external data server 108 owned by the same entity that owns and/or operates the agricultural intelligence computer system 130. For example, the agricultural intelligence computer system 130 may include a data server focused exclusively on a type of data that might otherwise be obtained from third party sources, such as weather data. In some embodiments, an external data server 108 may actually be incorporated within the system 130.

An agricultural apparatus 111 may have one or more remote sensors 112 fixed thereon, which sensors are communicatively coupled either directly or indirectly via agricultural apparatus 111 to the agricultural intelligence computer system 130 and are programmed or configured to send sensor data to agricultural intelligence computer system 130. Examples of agricultural apparatus 111 include tractors, combines, harvesters, planters, trucks, fertilizer equipment, aerial vehicles including unmanned aerial vehicles, and any other item of physical machinery or hardware, typically mobile machinery, and which may be used in tasks associated with agriculture. In some embodiments, a single unit of apparatus 111 may comprise a plurality of sensors 112 that are coupled locally in a network on the apparatus; controller area network (CAN) is example of such a network that can be installed in combines, harvesters, sprayers, and cultivators. Application controller 114 is communicatively coupled to agricultural intelligence computer system 130 via the network(s) 109 and is programmed or configured to receive one or more scripts that are used to control an operating parameter of an agricultural vehicle or implement from the agricultural intelligence computer system 130. For instance, a controller area network (CAN) bus interface may be used to enable communications from the agricultural intelligence computer system 130 to the agricultural apparatus 111, such as how the CLIMATE FIELDVIEW DRIVE, available from The Climate Corporation, San Francisco, Calif., is used. Sensor data may consist of the same type of information as field data 106. In some embodiments, remote sensors 112 may not be fixed to an agricultural apparatus 111 but may be remotely located in the field and may communicate with network 109.

The apparatus 111 may comprise a cab computer 115 that is programmed with a cab application, which may comprise a version or variant of the mobile application for device 104 that is further described in other sections herein. In an embodiment, cab computer 115 comprises a compact computer, often a tablet-sized computer or smartphone, with a graphical screen display, such as a color display, that is mounted within an operator's cab of the apparatus 111. Cab computer 115 may implement some or all of the operations and functions that are described further herein for the mobile computer device 104.

The network(s) 109 broadly represent any combination of one or more data communication networks including local area networks, wide area networks, internetworks or internets, using any of wireline or wireless links, including terrestrial or satellite links. The network(s) may be implemented by any medium or mechanism that provides for the exchange of data between the various elements of FIG. 1. The various elements of FIG. 1 may also have direct (wired or wireless) communications links. The sensors 112, controller 114, external data server computer 108, and other elements of the system each comprise an interface compatible with the network(s) 109 and are programmed or configured to use standardized protocols for communication across the networks such as TCP/IP, Bluetooth, CAN protocol and higher-layer protocols such as HTTP, TLS, and the like.

Agricultural intelligence computer system 130 is programmed or configured to receive field data 106 from field manager computing device 104, external data 110 from external data server computer 108, and sensor data from remote sensor 112. Agricultural intelligence computer system 130 may be further configured to host, use or execute one or more computer programs, other software elements, digitally programmed logic such as FPGAs or ASICs, or any combination thereof to perform translation and storage of data values, construction of digital models of one or more crops on one or more fields, generation of recommendations and notifications, and generation and sending of scripts to application controller 114, in the manner described further in other sections of this disclosure.

In an embodiment, agricultural intelligence computer system 130 is programmed with or comprises a communication layer 132, presentation layer 134, data management layer 140, hardware/virtualization layer 150, and model and field data repository 160. "Layer," in this context, refers to any combination of electronic digital interface circuits, microcontrollers, firmware such as drivers, and/or computer programs or other software elements.

Communication layer 132 may be programmed or configured to perform input/output interfacing functions including sending requests to field manager computing device 104, external data server computer 108, and remote sensor 112 for field data, external data, and sensor data respectively. Communication layer 132 may be programmed or configured to send the received data to model and field data repository 160 to be stored as field data 106.

Presentation layer 134 may be programmed or configured to generate a graphical user interface (GUI) to be displayed on field manager computing device 104, cab computer 115 or other computers that are coupled to the system 130 through the network 109. The GUI may comprise controls for inputting data to be sent to agricultural intelligence computer system 130, generating requests for models and/or recommendations, and/or displaying recommendations, notifications, models, and other field data.

Data management layer 140 may be programmed or configured to manage read operations and write operations involving the repository 160 and other functional elements of the system, including queries and result sets communicated between the functional elements of the system and the repository. Examples of data management layer 140 include JDBC, SQL server interface code, and/or HADOOP interface code, among others. Repository 160 may comprise a database. As used herein, the term "database" may refer to either a body of data, a relational database management system (RDBMS), or to both. As used herein, a database may comprise any collection of data including hierarchical databases, relational databases, flat file databases, object-relational databases, object oriented databases, distributed databases, and any other structured collection of records or data that is stored in a computer system. Examples of RDBMS's include, but are not limited to including, ORACLE®, MYSQL, IBM® DB2, MICROSOFT® SQL SERVER, SYBASE®, and POSTGRESQL databases. However, any database may be used that enables the systems and methods described herein.

When field data 106 is not provided directly to the agricultural intelligence computer system via one or more agricultural machines or agricultural machine devices that interacts with the agricultural intelligence computer system, the user may be prompted via one or more user interfaces on the user device (served by the agricultural intelligence computer system) to input such information. In an example embodiment, the user may specify identification data by accessing a map on the user device (served by the agricultural intelligence computer system) and selecting specific CLUs that have been graphically shown on the map. In an alternative embodiment, the user 102 may specify identification data by accessing a map on the user device (served by the agricultural intelligence computer system 130) and drawing boundaries of the field over the map. Such CLU selection or map drawings represent geographic identifiers. In alternative embodiments, the user may specify identification data by accessing field identification data (provided as shape files or in a similar format) from the U. S. Department of Agriculture Farm Service Agency or other source via the user device and providing such field identification data to the agricultural intelligence computer system.

In an example embodiment, the agricultural intelligence computer system 130 is programmed to generate and cause displaying a graphical user interface comprising a data manager for data input. After one or more fields have been identified using the methods described above, the data manager may provide one or more graphical user interface widgets which when selected can identify changes to the field, soil, crops, tillage, or nutrient practices. The data manager may include a timeline view, a spreadsheet view, and/or one or more editable programs.

Figure 5:
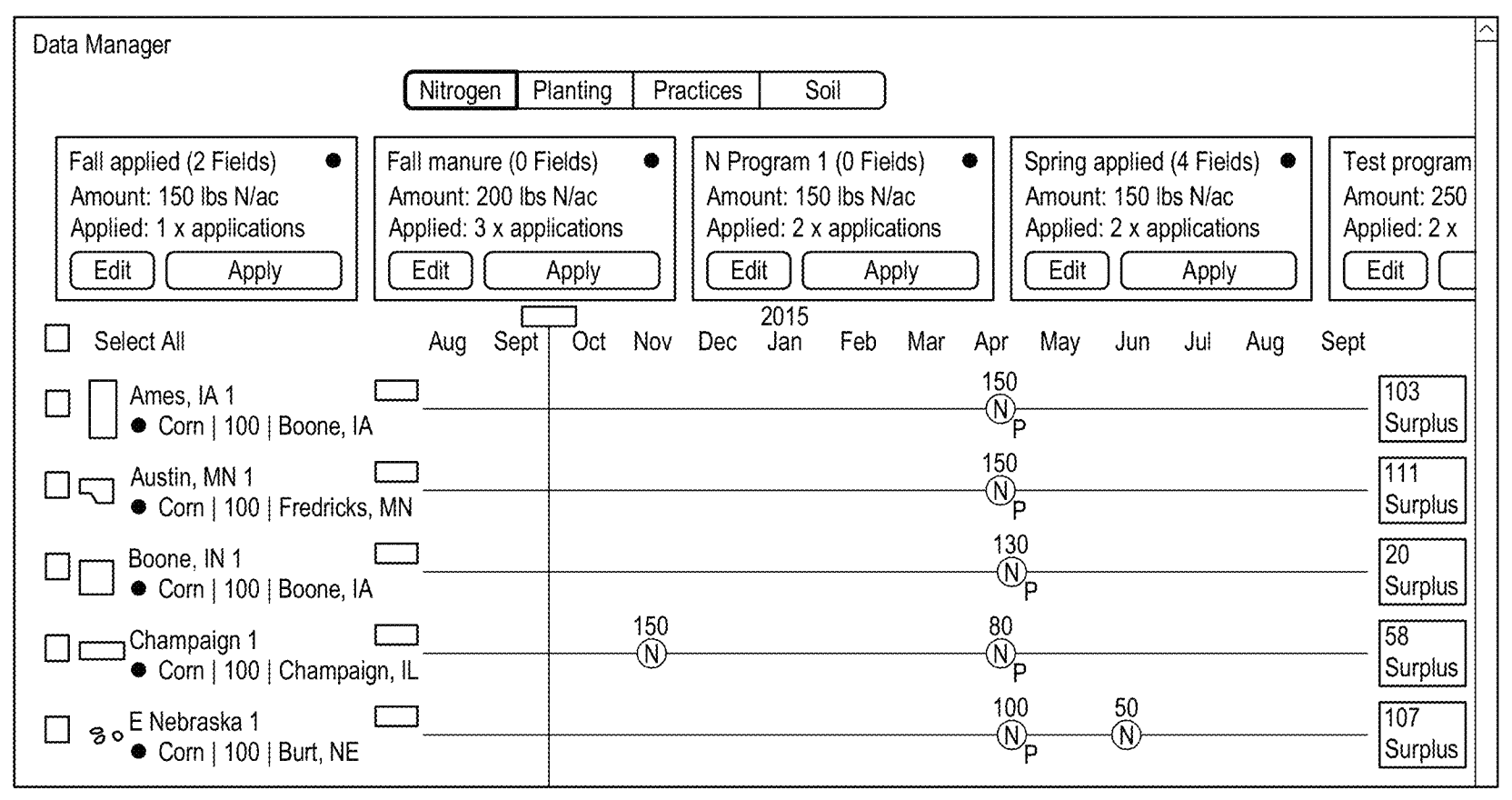

FIG. 5 depicts an example embodiment of a timeline view for data entry. Using the display depicted in FIG. 5, a user computer can input a selection of a particular field and a particular date for the addition of event. Events depicted at the top of the timeline may include Nitrogen, Planting, Practices, and Soil. To add a nitrogen application event, a user computer may provide input to select the nitrogen tab. The user computer may then select a location on the timeline for a particular field in order to indicate an application of nitrogen on the selected field. In response to receiving a selection of a location on the timeline for a particular field, the data manager may display a data entry overlay, allowing the user computer to input data pertaining to nitrogen applications, planting procedures, soil application, tillage procedures, irrigation practices, or other information relating to the particular field. For example, if a user computer selects a portion of the timeline and indicates an application of nitrogen, then the data entry overlay may include fields for inputting an amount of nitrogen applied, a date of application, a type of fertilizer used, and any other information related to the application of nitrogen.

In an embodiment, the data manager provides an interface for creating one or more programs. "Program," in this context, refers to a set of data pertaining to nitrogen applications, planting procedures, soil application, tillage procedures, irrigation practices, or other information that may be related to one or more fields, and that can be stored in digital data storage for reuse as a set in other operations. After a program has been created, it may be conceptually applied to one or more fields and references to the program may be stored in digital storage in association with data identifying the fields. Thus, instead of manually entering identical data relating to the same nitrogen applications for multiple different fields, a user computer may create a program that indicates a particular application of nitrogen and then apply the program to multiple different fields. For example, in the timeline view of FIG. 5, the top two timelines have the "Spring applied" program selected, which includes an application of 150 lbs N/ac in early April. The data manager may provide an interface for editing a program. In an embodiment, when a particular program is edited, each field that has selected the particular program is edited. For example, in FIG. 5, if the "Spring applied" program is edited to reduce the application of nitrogen to 130 lbs N/ac, the top two fields may be updated with a reduced application of nitrogen based on the edited program.

In an embodiment, in response to receiving edits to a field that has a program selected, the data manager removes the correspondence of the field to the selected program. For example, if a nitrogen application is added to the top field in FIG. 5, the interface may update to indicate that the "Spring applied" program is no longer being applied to the top field. While the nitrogen application in early April may remain, updates to the "Spring applied" program would not alter the April application of nitrogen.

FIG. 6 depicts an example embodiment of a spreadsheet view for data entry. Using the display depicted in FIG. 6, a user can create and edit information for one or more fields. The data manager may include spreadsheets for inputting information with respect to Nitrogen, Planting, Practices, and Soil as depicted in FIG. 6. To edit a particular entry, a user computer may select the particular entry in the spreadsheet and update the values. For example, FIG. 6 depicts an in-progress update to a target yield value for the second field. Additionally, a user computer may select one or more fields in order to apply one or more programs. In response to receiving a selection of a program for a particular field, the data manager may automatically complete the entries for the particular field based on the selected program. As with the timeline view, the data manager may update the entries for each field associated with a particular program in response to receiving an update to the program. Additionally, the data manager may remove the correspondence of the selected program to the field in response to receiving an edit to one of the entries for the field.

In an embodiment, model and field data is stored in model and field data repository 160. Model data comprises data models created for one or more fields. For example, a crop model may include a digitally constructed model of the development of a crop on the one or more fields. "Model," in this context, refers to an electronic digitally stored set of executable instructions and data values, associated with one another, which are capable of receiving and responding to a programmatic or other digital call, invocation, or request for resolution based upon specified input values, to yield one or more stored or calculated output values that can serve as the basis of computer-implemented recommendations, output data displays, or machine control, among other things. Persons of skill in the field find it convenient to express models using mathematical equations, but that form of expression does not confine the models disclosed herein to abstract concepts; instead, each model herein has a practical application in a computer in the form of stored executable instructions and data that implement the model using the computer. The model may include a model of past events on the one or more fields, a model of the current status of the one or more fields, and/or a model of predicted events on the one or more fields. Model and field data may be stored in data structures in memory, rows in a database table, in flat files or spreadsheets, or other forms of stored digital data.

In some embodiments, agricultural intelligence computer system 130 is programmed with or comprises a soil analysis server ("server") 170. The server 170 is further configured to comprise a soil element concentration analysis component 172 and a client interface 174. Each of the soil element concentration analysis component 172 and the client interface 174 may be implemented as sequences of stored program instructions. In some embodiments, the soil element concentration analysis component 172 is programmed to receive input data from one or more sources and output current concentration levels of a target analyte in the soil or recommendations for adjusting the current concentration levels. Input data to the soil element concentration analysis component 172 can include data generated by the mobile soil analysis system introduced above and to be further discussed in in FIG. 8, which can comprise one or more of the agricultural apparatus 111, the application controller 114, and the remote sensor 112. An example of such data would be current nitrate concentration levels in certain soil samples. Additional input data can include data received from user computers, such as the field manager computing device 104 or the cab computer 115, or from the data server computer 108, or other data that have been stored in the model data field data repository 160, such as expected crop yield levels, soil nutrient loss history, historical weather reports or weather forecasts, or records of applying other types of soil nutrients. Output data from the soil element concentration analysis component 172 can include when and how to adjust concentration levels of certain soil nutrients or other elements as well as where such adjustment should be applied. Such data can be communicated to the user computers or other remote computers.

In some embodiments, the client interface 174 is configured to manage communication with the mobile soil analysis system or a user computer over a communication network, through the communication layer 132. The communication can include receiving instructions to start real-time field measurements and desired soil condition or production level from a user computer, sending instructions to the mobile soil analysis system for performing real-time measurements of soil element concentration levels, receiving the soil measurements from the mobile soil analysis system, and sending results of analyzing the soil measurements with respect to the desired soil condition or production level to the user computer.

Each component of the server 170 comprises a set of one or more pages of main memory, such as RAM, in the agricultural intelligence computer system 130 into which executable instructions have been loaded and which when executed cause the agricultural intelligence computing system to perform the functions or operations that are described herein with reference to those modules. For example, the soil element concentration analysis component 172 may comprise a set of pages in RAM that contain instructions which when executed cause performing soil element concentration analysis described herein. The instructions may be in machine executable code in the instruction set of a CPU and may have been compiled based upon source code written in JAVA, C, C++, OBJECTIVE-C, or any other human-readable programming language or environment, alone or in combination with scripts in JAVASCRIPT, other scripting languages and other programming source text. The term "pages" is intended to refer broadly to any region within main memory and the specific terminology used in a system may vary depending on the memory architecture or processor architecture. In another embodiment, each of the components in the server 170 also may represent one or more files or projects of source code that are digitally stored in a mass storage device such as non-volatile RAM or disk storage, in the agricultural intelligence computer system 130 or a separate repository system, which when compiled or interpreted cause generating executable instructions which when executed cause the agricultural intelligence computing system to perform the functions or operations that are described herein with reference to those modules. In other words, the drawing figure may represent the manner in which programmers or software developers organize and arrange source code for later compilation into an executable, or interpretation into bytecode or the equivalent, for execution by the agricultural intelligence computer system 130.

Figure 4:
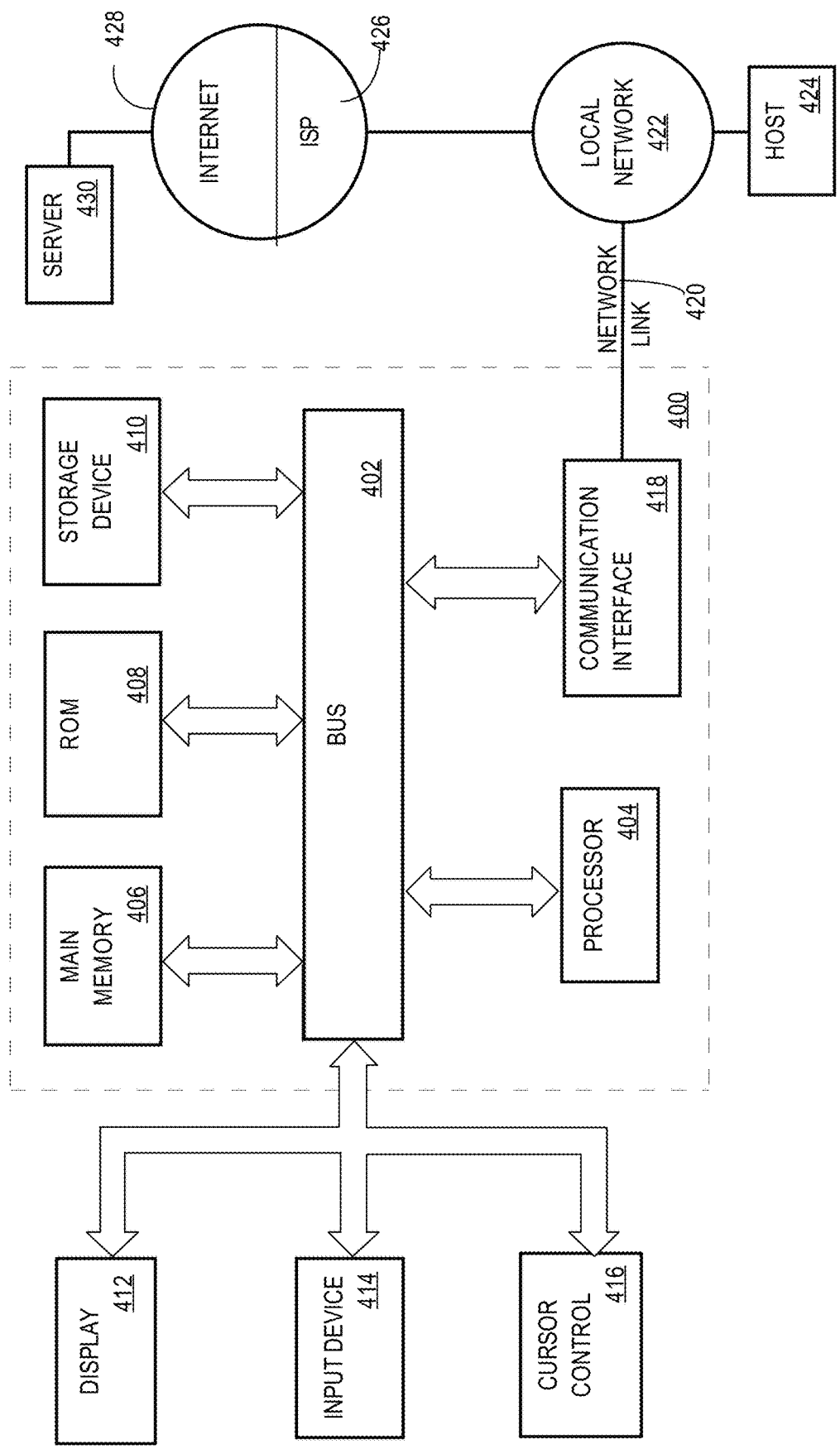
FIG. 4 is a block diagram that illustrates a computer system upon which an embodiment of the invention may be implemented.

Hardware/virtualization layer 150 comprises one or more central processing units (CPUs), memory controllers, and other devices, components, or elements of a computer system such as volatile or non-volatile memory, non-volatile storage such as disk, and I/O devices or interfaces as illustrated and described, for example, in connection with FIG. 4. The layer 150 also may comprise programmed instructions that are configured to support virtualization, containerization, or other technologies.

For purposes of illustrating a clear example, FIG. 1 shows a limited number of instances of certain functional elements. However, in other embodiments, there may be any number of such elements. For example, embodiments may use thousands or millions of different mobile computing devices 104 associated with different users. Further, the system 130 and/or external data server computer 108 may be implemented using two or more processors, cores, clusters, or instances of physical machines or virtual machines, configured in a discrete location or co-located with other elements in a datacenter, shared computing facility or cloud computing facility.

2.2. Application Program Overview

In an embodiment, the implementation of the functions described herein using one or more computer programs or other software elements that are loaded into and executed using one or more general-purpose computers will cause the general-purpose computers to be configured as a particular machine or as a computer that is specially adapted to perform the functions described herein. Further, each of the flow diagrams that are described further herein may serve, alone or in combination with the descriptions of processes and functions in prose herein, as algorithms, plans or directions that may be used to program a computer or logic to implement the functions that are described. In other words, all the prose text herein, and all the drawing figures, together are intended to provide disclosure of algorithms, plans or directions that are sufficient to permit a skilled person to program a computer to perform the functions that are described herein, in combination with the skill and knowledge of such a person given the level of skill that is appropriate for inventions and disclosures of this type.

In an embodiment, user 102 interacts with agricultural intelligence computer system 130 using field manager computing device 104 configured with an operating system and one or more application programs or apps; the field manager computing device 104 also may interoperate with the agricultural intelligence computer system independently and automatically under program control or logical control and direct user interaction is not always required. Field manager computing device 104 broadly represents one or more of a smart phone, PDA, tablet computing device, laptop computer, desktop computer, workstation, or any other computing device capable of transmitting and receiving information and performing the functions described herein. Field manager computing device 104 may communicate via a network using a mobile application stored on field manager computing device 104, and in some embodiments, the device may be coupled using a cable 113 or connector to the sensor 112 and/or controller 114. A particular user 102 may own, operate or possess and use, in connection with system 130, more than one field manager computing device 104 at a time.

The mobile application may provide client-side functionality, via the network to one or more mobile computing devices. In an example embodiment, field manager computing device 104 may access the mobile application via a web browser or a local client application or app. Field manager computing device 104 may transmit data to, and receive data from, one or more front-end servers, using web-based protocols or formats such as HTTP, XML, and/or JSON, or app-specific protocols. In an example embodiment, the data may take the form of requests and user information input, such as field data, into the mobile computing device. In some embodiments, the mobile application interacts with location tracking hardware and software on field manager computing device 104 which determines the location of field manager computing device 104 using standard tracking techniques such as multilateration of radio signals, the global positioning system (GPS), WiFi positioning systems, or other methods of mobile positioning. In some cases, location data or other data associated with the device 104, user 102, and/or user account(s) may be obtained by queries to an operating system of the device or by requesting an app on the device to obtain data from the operating system.

In an embodiment, field manager computing device 104 sends field data 106 to agricultural intelligence computer system 130 comprising or including, but not limited to, data values representing one or more of: a geographical location of the one or more fields, tillage information for the one or more fields, crops planted in the one or more fields, and soil data extracted from the one or more fields. Field manager computing device 104 may send field data 106 in response to user input from user 102 specifying the data values for the one or more fields. Additionally, field manager computing device 104 may automatically send field data 106 when one or more of the data values becomes available to field manager computing device 104. For example, field manager computing device 104 may be communicatively coupled to remote sensor 112 and/or application controller 114 which include an irrigation sensor and/or irrigation controller. In response to receiving data indicating that application controller 114 released water onto the one or more fields, field manager computing device 104 may send field data 106 to agricultural intelligence computer system 130 indicating that water was released on the one or more fields. Field data 106 identified in this disclosure may be input and communicated using electronic digital data that is communicated between computing devices using parameterized URLs over HTTP, or another suitable communication or messaging protocol.

A commercial example of the mobile application is CLIMATE FIELDVIEW, commercially available from The Climate Corporation, San Francisco, Calif. The CLIMATE FIELDVIEW application, or other applications, may be modified, extended, or adapted to include features, functions, and programming that have not been disclosed earlier than the filing date of this disclosure. In one embodiment, the mobile application comprises an integrated software platform that allows a grower to make fact-based decisions for their operation because it combines historical data about the grower's fields with any other data that the grower wishes to compare. The combinations and comparisons may be performed in real time and are based upon scientific models that provide potential scenarios to permit the grower to make better, more informed decisions.

FIG. 2 illustrates two views of an example logical organization of sets of instructions in main memory when an example mobile application is loaded for execution. In FIG. 2, each named element represents a region of one or more pages of RAM or other main memory, or one or more blocks of disk storage or other non-volatile storage, and the programmed instructions within those regions. In one embodiment, in view (a), a mobile computer application 200 comprises account-fields-data ingestion-sharing instructions 202, overview and alert instructions 204, digital map book instructions 206, seeds and planting instructions 208, nitrogen instructions 210, weather instructions 212, field health instructions 214, and performance instructions 216.

In one embodiment, a mobile computer application 200 comprises account, fields, data ingestion, sharing instructions 202 which are programmed to receive, translate, and ingest field data from third party systems via manual upload or APIs. Data types may include field boundaries, yield maps, as-planted maps, soil test results, as-applied maps, and/or management zones, among others. Data formats may include shape files, native data formats of third parties, and/or farm management information system (FMIS) exports, among others. Receiving data may occur via manual upload, e-mail with attachment, external APIs that push data to the mobile application, or instructions that call APIs of external systems to pull data into the mobile application. In one embodiment, mobile computer application 200 comprises a data inbox. In response to receiving a selection of the data inbox, the mobile computer application 200 may display a graphical user interface for manually uploading data files and importing uploaded files to a data manager.

In one embodiment, digital map book instructions 206 comprise field map data layers stored in device memory and are programmed with data visualization tools and geospatial field notes. This provides growers with convenient information close at hand for reference, logging and visual insights into field performance. In one embodiment, overview and alert instructions 204 are programmed to provide an operation-wide view of what is important to the grower, and timely recommendations to take action or focus on particular issues. This permits the grower to focus time on what needs attention, to save time and preserve yield throughout the season. In one embodiment, seeds and planting instructions 208 are programmed to provide tools for seed selection, hybrid placement, and script creation, including variable rate (VR) script creation, based upon scientific models and empirical data. This enables growers to maximize yield or return on investment through optimized seed purchase, placement and population.

In one embodiment, script generation instructions 205 are programmed to provide an interface for generating scripts, including variable rate (VR) fertility scripts. The interface enables growers to create scripts for field implements, such as nutrient applications, planting, and irrigation. For example, a planting script interface may comprise tools for identifying a type of seed for planting. Upon receiving a selection of the seed type, mobile computer application 200 may display one or more fields broken into management zones, such as the field map data layers created as part of digital map book instructions 206. In one embodiment, the management zones comprise soil zones along with a panel identifying each soil zone and a soil name, texture, drainage for each zone, or other field data. Mobile computer application 200 may also display tools for editing or creating such, such as graphical tools for drawing management zones, such as soil zones, over a map of one or more fields. Planting procedures may be applied to all management zones or different planting procedures may be applied to different subsets of management zones. When a script is created, mobile computer application 200 may make the script available for download in a format readable by an application controller, such as an archived or compressed format. Additionally, and/or alternatively, a script may be sent directly to cab computer 115 from mobile computer application 200 and/or uploaded to one or more data servers and stored for further use.

In one embodiment, nitrogen instructions 210 are programmed to provide tools to inform nitrogen decisions by visualizing the availability of nitrogen to crops. This enables growers to maximize yield or return on investment through optimized nitrogen application during the season. Example programmed functions include displaying images such as SSURGO images to enable drawing of fertilizer application zones and/or images generated from subfield soil data, such as data obtained from sensors, at a high spatial resolution (as fine as millimeters or smaller depending on sensor proximity and resolution); upload of existing grower-defined zones; providing a graph of plant nutrient availability and/or a map to enable tuning application(s) of nitrogen across multiple zones; output of scripts to drive machinery; tools for mass data entry and adjustment; and/or maps for data visualization, among others. "Mass data entry," in this context, may mean entering data once and then applying the same data to multiple fields and/or zones that have been defined in the system; example data may include nitrogen application data that is the same for many fields and/or zones of the same grower, but such mass data entry applies to the entry of any type of field data into the mobile computer application 200. For example, nitrogen instructions 210 may be programmed to accept definitions of nitrogen application and practices programs and to accept user input specifying to apply those programs across multiple fields. "Nitrogen application programs," in this context, refers to stored, named sets of data that associates: a name, color code or other identifier, one or more dates of application, types of material or product for each of the dates and amounts, method of application or incorporation such as injected or broadcast, and/or amounts or rates of application for each of the dates, crop or hybrid that is the subject of the application, among others. "Nitrogen practices programs," in this context, refer to stored, named sets of data that associates: a practices name; a previous crop; a tillage system; a date of primarily tillage; one or more previous tillage systems that were used; one or more indicators of application type, such as manure, that were used. Nitrogen instructions 210 also may be programmed to generate and cause displaying a nitrogen graph, which indicates projections of plant use of the specified nitrogen and whether a surplus or shortfall is predicted; in some embodiments, different color indicators may signal a magnitude of surplus or magnitude of shortfall. In one embodiment, a nitrogen graph comprises a graphical display in a computer display device comprising a plurality of rows, each row associated with and identifying a field; data specifying what crop is planted in the field, the field size, the field location, and a graphic representation of the field perimeter; in each row, a timeline by month with graphic indicators specifying each nitrogen application and amount at points correlated to month names; and numeric and/or colored indicators of surplus or shortfall, in which color indicates magnitude.

In one embodiment, the nitrogen graph may include one or more user input features, such as dials or slider bars, to dynamically change the nitrogen planting and practices programs so that a user may optimize his nitrogen graph. The user may then use his optimized nitrogen graph and the related nitrogen planting and practices programs to implement one or more scripts, including variable rate (VR)

fertility scripts. Nitrogen instructions 210 also may be programmed to generate and cause displaying a nitrogen map, which indicates projections of plant use of the specified nitrogen and whether a surplus or shortfall is predicted; in some embodiments, different color indicators may signal a magnitude of surplus or magnitude of shortfall. The nitrogen map may display projections of plant use of the specified nitrogen and whether a surplus or shortfall is predicted for different times in the past and the future (such as daily, weekly, monthly or yearly) using numeric and/or colored indicators of surplus or shortfall, in which color indicates magnitude. In one embodiment, the nitrogen map may include one or more user input features, such as dials or slider bars, to dynamically change the nitrogen planting and practices programs so that a user may optimize his nitrogen map, such as to obtain a preferred amount of surplus to shortfall. The user may then use his optimized nitrogen map and the related nitrogen planting and practices programs to implement one or more scripts, including variable rate (VR) fertility scripts. In other embodiments, similar instructions to the nitrogen instructions 210 could be used for application of other nutrients (such as phosphorus and potassium), application of pesticide, and irrigation programs.

In one embodiment, weather instructions 212 are programmed to provide field-specific recent weather data and forecasted weather information. This enables growers to save time and have an efficient integrated display with respect to daily operational decisions.

In one embodiment, field health instructions 214 are programmed to provide timely remote sensing images highlighting in-season crop variation and potential concerns. Example programmed functions include cloud checking, to identify possible clouds or cloud shadows; determining nitrogen indices based on field images; graphical visualization of scouting layers, including, for example, those related to field health, and viewing and/or sharing of scouting notes; and/or downloading satellite images from multiple sources and prioritizing the images for the grower, among others.

In one embodiment, performance instructions 216 are programmed to provide reports, analysis, and insight tools using on-farm data for evaluation, insights and decisions. This enables the grower to seek improved outcomes for the next year through fact-based conclusions about why return on investment was at prior levels, and insight into yield-limiting factors. The performance instructions 216 may be programmed to communicate via the network(s) 109 to back-end analytics programs executed at agricultural intelligence computer system 130 and/or external data server computer 108 and configured to analyze metrics such as yield, yield differential, hybrid, population, SSURGO zone, soil test properties, or elevation, among others. Programmed reports and analysis may include yield variability analysis, treatment effect estimation, benchmarking of yield and other metrics against other growers based on anonymized data collected from many growers, or data for seeds and planting, among others.

Applications having instructions configured in this way may be implemented for different computing device platforms while retaining the same general user interface appearance. For example, the mobile application may be programmed for execution on tablets, smartphones, or server computers that are accessed using browsers at client computers. Further, the mobile application as configured for tablet computers or smartphones may provide a full app experience or a cab app experience that is suitable for the display and processing capabilities of cab computer 115. For example, referring now to view (b) of FIG. 2, in one embodiment a cab computer application 220 may comprise maps-cab instructions 222, remote view instructions 224, data collect and transfer instructions 226, machine alerts instructions 228, script transfer instructions 230, and scouting-cab instructions 232. The code base for the instructions of view (b) may be the same as for view (a) and executables implementing the code may be programmed to detect the type of platform on which they are executing and to expose, through a graphical user interface, only those functions that are appropriate to a cab platform or full platform. This approach enables the system to recognize the distinctly different user experience that is appropriate for an in-cab environment and the different technology environment of the cab. The maps-cab instructions 222 may be programmed to provide map views of fields, farms or regions that are useful in directing machine operation. The remote view instructions 224 may be programmed to turn on, manage, and provide views of machine activity in real-time or near real-time to other computing devices connected to the system 130 via wireless networks, wired connectors or adapters, and the like. The data collect and transfer instructions 226 may be programmed to turn on, manage, and provide transfer of data collected at sensors and controllers to the system 130 via wireless networks, wired connectors or adapters, and the like. The machine alerts instructions 228 may be programmed to detect issues with operations of the machine or tools that are associated with the cab and generate operator alerts. The script transfer instructions 230 may be configured to transfer in scripts of instructions that are configured to direct machine operations or the collection of data. The scouting-cab instructions 232 may be programmed to display location-based alerts and information received from the system 130 based on the location of the field manager computing device 104, agricultural apparatus 111, or sensors 112 in the field and ingest, manage, and provide transfer of location-based scouting observations to the system 130 based on the location of the agricultural apparatus 111 or sensors 112 in the field.

2.3. Data Ingest to the Computer System

In an embodiment, external data server computer 108 stores external data 110, including soil data representing soil composition for the one or more fields and weather data representing temperature and precipitation on the one or more fields. The weather data may include past and present weather data as well as forecasts for future weather data. In an embodiment, external data server computer 108 comprises a plurality of servers hosted by different entities. For example, a first server may contain soil composition data while a second server may include weather data. Additionally, soil composition data may be stored in multiple servers. For example, one server may store data representing percentage of sand, silt, and clay in the soil while a second server may store data representing percentage of organic matter (OM) in the soil.

In an embodiment, remote sensor 112 comprises one or more sensors that are programmed or configured to produce one or more observations. Remote sensor 112 may be aerial sensors, such as satellites, vehicle sensors, planting equipment sensors, tillage sensors, fertilizer or insecticide application sensors, harvester sensors, and any other implement capable of receiving data from the one or more fields. In an embodiment, application controller 114 is programmed or configured to receive instructions from agricultural intelligence computer system 130. Application controller 114 may also be programmed or configured to control an operating parameter of an agricultural vehicle or implement. For example, an application controller may be programmed or configured to control an operating parameter of a vehicle, such as a tractor, planting equipment, tillage equipment, fertilizer or insecticide equipment, harvester equipment, or other farm implements such as a water valve. Other embodiments may use any combination of sensors and controllers, of which the following are merely selected examples.

The system 130 may obtain or ingest data under user 102 control, on a mass basis from a large number of growers who have contributed data to a shared database system. This form of obtaining data may be termed "manual data ingest" as one or more user-controlled computer operations are requested or triggered to obtain data for use by the system 130. As an example, the CLIMATE FIELDVIEW application, commercially available from The Climate Corporation, San Francisco, Calif., may be operated to export data to system 130 for storing in the repository 160.

For example, seed monitor systems can both control planter apparatus components and obtain planting data, including signals from seed sensors via a signal harness that comprises a CAN backbone and point-to-point connections for registration and/or diagnostics. Seed monitor systems can be programmed or configured to display seed spacing, population and other information to the user via the cab computer 115 or other devices within the system 130. Examples are disclosed in U.S. Pat. No. 8,738,243 and US Pat. Pub. 20150094916, and the present disclosure assumes knowledge of those other patent disclosures.

Likewise, yield monitor systems may contain yield sensors for harvester apparatus that send yield measurement data to the cab computer 115 or other devices within the system 130. Yield monitor systems may utilize one or more remote sensors 112 to obtain grain moisture measurements in a combine or other harvester and transmit these measurements to the user via the cab computer 115 or other devices within the system 130.

In an embodiment, examples of sensors 112 that may be used with any moving vehicle or apparatus of the type described elsewhere herein include kinematic sensors and position sensors. Kinematic sensors may comprise any of speed sensors such as radar or wheel speed sensors, accelerometers, or gyros. Position sensors may comprise GPS receivers or transceivers, or WiFi-based position or mapping apps that are programmed to determine location based upon nearby WiFi hotspots, among others.

In an embodiment, examples of sensors 112 that may be used with tractors or other moving vehicles include engine speed sensors, fuel consumption sensors, area counters or distance counters that interact with GPS or radar signals, PTO (power take-off) speed sensors, tractor hydraulics sensors configured to detect hydraulics parameters such as pressure or flow, and/or and hydraulic pump speed, wheel speed sensors or wheel slippage sensors. In an embodiment, examples of controllers 114 that may be used with tractors include hydraulic directional controllers, pressure controllers, and/or flow controllers; hydraulic pump speed controllers; speed controllers or governors; hitch position controllers; or wheel position controllers provide automatic steering.

In an embodiment, examples of sensors 112 that may be used with seed planting equipment such as planters, drills, or air seeders include seed sensors, which may be optical, electromagnetic, or impact sensors; downforce sensors such as load pins, load cells, pressure sensors; soil property sensors such as reflectivity sensors, moisture sensors, electrical conductivity sensors, optical residue sensors, or temperature sensors; component operating criteria sensors such as planting depth sensors, downforce cylinder pressure sensors, seed disc speed sensors, seed drive motor encoders, seed conveyor system speed sensors, or vacuum level sensors; or pesticide application sensors such as optical or other electromagnetic sensors, or impact sensors. In an embodiment, examples of controllers 114 that may be used with such seed planting equipment include: toolbar fold controllers, such as controllers for valves associated with hydraulic cylinders; downforce controllers, such as controllers for valves associated with pneumatic cylinders, airbags, or hydraulic cylinders, and programmed for applying downforce to individual row units or an entire planter frame; planting depth controllers, such as linear actuators; metering controllers, such as electric seed meter drive motors, hydraulic seed meter drive motors, or swath control clutches; hybrid selection controllers, such as seed meter drive motors, or other actuators programmed for selectively allowing or preventing seed or an air-seed mixture from delivering seed to or from seed meters or central bulk hoppers; metering controllers, such as electric seed meter drive motors, or hydraulic seed meter drive motors; seed conveyor system controllers, such as controllers for a belt seed delivery conveyor motor; marker controllers, such as a controller for a pneumatic or hydraulic actuator; or pesticide application rate controllers, such as metering drive controllers, orifice size or position controllers.

In an embodiment, examples of sensors 112 that may be used with tillage equipment include position sensors for tools such as shanks or discs; tool position sensors for such tools that are configured to detect depth, gang angle, or lateral spacing; downforce sensors; or draft force sensors. In an embodiment, examples of controllers 114 that may be used with tillage equipment include downforce controllers or tool position controllers, such as controllers configured to control tool depth, gang angle, or lateral spacing.

In an embodiment, examples of sensors 112 that may be used in relation to apparatus for applying fertilizer, insecticide, fungicide and the like, such as on-planter starter fertilizer systems, subsoil fertilizer applicators, or fertilizer sprayers, include: fluid system criteria sensors, such as flow sensors or pressure sensors; sensors indicating which spray head valves or fluid line valves are open; sensors associated with tanks, such as fill level sensors; sectional or system-wide supply line sensors, or row-specific supply line sensors; or kinematic sensors such as accelerometers disposed on sprayer booms. In an embodiment, examples of controllers 114 that may be used with such apparatus include pump speed controllers; valve controllers that are programmed to control pressure, flow, direction, PWM and the like; or position actuators, such as for boom height, subsoiler depth, or boom position.

In an embodiment, examples of sensors 112 that may be used with harvesters include yield monitors, such as impact plate strain gauges or position sensors, capacitive flow sensors, load sensors, weight sensors, or torque sensors associated with elevators or augers, or optical or other electromagnetic grain height sensors; grain moisture sensors, such as capacitive sensors; grain loss sensors, including impact, optical, or capacitive sensors; header operating criteria sensors such as header height, header type, deck plate gap, feeder speed, and reel speed sensors; separator operating criteria sensors, such as concave clearance, rotor speed, shoe clearance, or chaffer clearance sensors; auger sensors for position, operation, or speed; or engine speed sensors. In an embodiment, examples of controllers 114 that may be used with harvesters include header operating criteria controllers for elements such as header height, header type, deck plate gap, feeder speed, or reel speed; separator operating criteria controllers for features such as concave clearance, rotor speed, shoe clearance, or chaffer clearance; or controllers for auger position, operation, or speed.

In an embodiment, examples of sensors 112 that may be used with grain carts include weight sensors, or sensors for auger position, operation, or speed. In an embodiment, examples of controllers 114 that may be used with grain carts include controllers for auger position, operation, or speed.

In an embodiment, examples of sensors 112 and controllers 114 may be installed in unmanned aerial vehicle (UAV) apparatus or "drones." Such sensors may include cameras with detectors effective for any range of the electromagnetic spectrum including visible light, infrared, ultraviolet, near-infrared (NIR), and the like; accelerometers; altimeters; temperature sensors; humidity sensors; pitot tube sensors or other airspeed or wind velocity sensors; battery life sensors; or radar emitters and reflected radar energy detection apparatus; other electromagnetic radiation emitters and reflected electromagnetic radiation detection apparatus. Such controllers may include guidance or motor control apparatus, control surface controllers, camera controllers, or controllers programmed to turn on, operate, obtain data from, manage and configure any of the foregoing sensors. Examples are disclosed in U.S. patent application Ser. No. 14/831,165 and the present disclosure assumes knowledge of that other patent disclosure.

In an embodiment, sensors 112 and controllers 114 may be affixed to soil sampling and measurement apparatus that is configured or programmed to sample soil and perform soil chemistry tests, soil moisture tests, and other tests pertaining to soil. For example, the apparatus disclosed in U.S. Pat. Nos. 8,767,194 and 8,712,148 may be used, and the present disclosure assumes knowledge of those patent disclosures.

In an embodiment, sensors 112 and controllers 114 may comprise weather devices for monitoring weather conditions of fields. For example, the apparatus disclosed in U.S. Provisional Application No. 62/154,207, filed on Apr. 29, 2015, U.S. Provisional Application No. 62/175,160, filed on Jun. 12, 2015, U.S. Provisional Application No. 62/198,060, filed on Jul. 28, 2015, and U.S. Provisional Application No. 62/220,852, filed on Sep. 18, 2015, may be used, and the present disclosure assumes knowledge of those patent disclosures.

2.4. Process Overview-Agronomic Model Training

In an embodiment, the agricultural intelligence computer system 130 is programmed or configured to create an agronomic model. In this context, an agronomic model is a data structure in memory of the agricultural intelligence computer system 130 that comprises field data 106, such as identification data and harvest data for one or more fields. The agronomic model may also comprise calculated agronomic properties which describe either conditions which may affect the growth of one or more crops on a field, or properties of the one or more crops, or both. Additionally, an agronomic model may comprise recommendations based on agronomic factors such as crop recommendations, irrigation recommendations, planting recommendations, fertilizer recommendations, fungicide recommendations, pesticide recommendations, harvesting recommendations and other crop management recommendations. The agronomic factors may also be used to estimate one or more crop related results, such as agronomic yield. The agronomic yield of a crop is an estimate of quantity of the crop that is produced, or in some examples the revenue or profit obtained from the produced crop.

In an embodiment, the agricultural intelligence computer system 130 may use a preconfigured agronomic model to calculate agronomic properties related to currently received location and crop information for one or more fields. The preconfigured agronomic model is based upon previously processed field data, including but not limited to, identification data, harvest data, fertilizer data, and weather data. The preconfigured agronomic model may have been cross validated to ensure accuracy of the model. Cross validation may include comparison to ground truthing that compares predicted results with actual results on a field, such as a comparison of precipitation estimate with a rain gauge or sensor providing weather data at the same or nearby location or an estimate of nitrogen content with a soil sample measurement.

Figure 3:
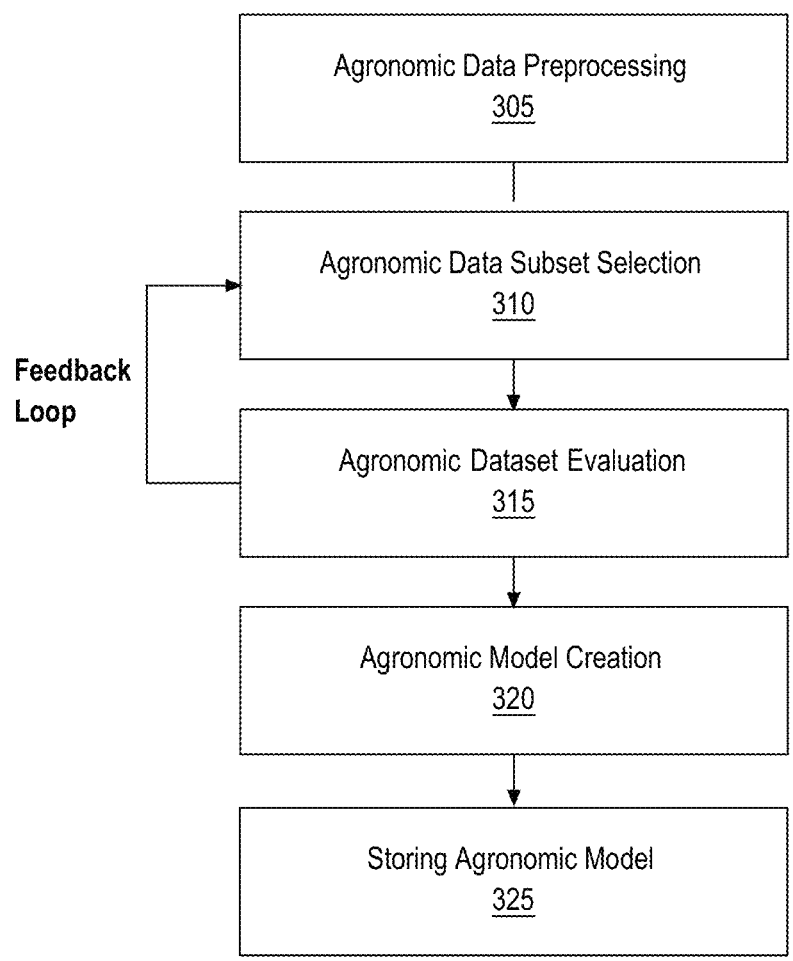
FIG. 3 illustrates a programmed process by which the agricultural intelligence computer system generates one or more preconfigured agronomic models using agronomic data provided by one or more data sources.

FIG. 3 illustrates a programmed process by which the agricultural intelligence computer system generates one or more preconfigured agronomic models using field data provided by one or more data sources. FIG. 3 may serve as an algorithm or instructions for programming the functional elements of the agricultural intelligence computer system 130 to perform the operations that are now described.

At block 305, the agricultural intelligence computer system 130 is configured or programmed to implement agronomic data preprocessing of field data received from one or more data sources. The field data received from one or more data sources may be preprocessed for the purpose of removing noise, distorting effects, and confounding factors within the agronomic data including measured outliers that could adversely affect received field data values. Embodiments of agronomic data preprocessing may include, but are not limited to, removing data values commonly associated with outlier data values, specific measured data points that are known to unnecessarily skew other data values, data smoothing, aggregation, or sampling techniques used to remove or reduce additive or multiplicative effects from noise, and other filtering or data derivation techniques used to provide clear distinctions between positive and negative data inputs.

At block 310, the agricultural intelligence computer system 130 is configured or programmed to perform data subset selection using the preprocessed field data in order to identify datasets useful for initial agronomic model generation. The agricultural intelligence computer system 130 may implement data subset selection techniques including, but not limited to, a genetic algorithm method, an all subset models method, a sequential search method, a stepwise regression method, a particle swarm optimization method, and an ant colony optimization method. For example, a genetic algorithm selection technique uses an adaptive heuristic search algorithm, based on evolutionary principles of natural selection and genetics, to determine and evaluate datasets within the preprocessed agronomic data.

At block 315, the agricultural intelligence computer system 130 is configured or programmed to implement field dataset evaluation. In an embodiment, a specific field dataset is evaluated by creating an agronomic model and using specific quality thresholds for the created agronomic model. Agronomic models may be compared and/or validated using one or more comparison techniques, such as, but not limited to, root mean square error with leave-one-out cross validation (RMSECV), mean absolute error, and mean percentage error. For example, RMSECV can cross validate agronomic models by comparing predicted agronomic property values created by the agronomic model against historical agronomic property values collected and analyzed. In an embodiment, the agronomic dataset evaluation logic is used as a feedback loop where agronomic datasets that do not meet configured quality thresholds are used during future data subset selection steps (block 310).

At block 320, the agricultural intelligence computer system 130 is configured or programmed to implement agronomic model creation based upon the cross validated agronomic datasets. In an embodiment, agronomic model creation may implement multivariate regression techniques to create preconfigured agronomic data models.

At block 325, the agricultural intelligence computer system 130 is configured or programmed to store the preconfigured agronomic data models for future field data evaluation.

2.5. Implementation Example—Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

For example, FIG. 4 is a block diagram that illustrates a computer system 400 upon which an embodiment of the invention may be implemented. Computer system 400 includes a bus 402 or other communication mechanism for communicating information, and a hardware processor 404 coupled with bus 402 for processing information. Hardware processor 404 may be, for example, a general purpose microprocessor.

Computer system 400 also includes a main memory 406, such as a random access memory (RAM) or other dynamic storage device, coupled to bus 402 for storing information and instructions to be executed by processor 404. Main memory 406 also may be used for storing temporary variables or other intermediate information during execution of instructions to be executed by processor 404. Such instructions, when stored in non-transitory storage media accessible to processor 404, render computer system 400 into a special-purpose machine that is customized to perform the operations specified in the instructions.

Computer system 400 further includes a read only memory (ROM) 408 or other static storage device coupled to bus 402 for storing static information and instructions for processor 404. A storage device 410, such as a magnetic disk, optical disk, or solid-state drive is provided and coupled to bus 402 for storing information and instructions.

Computer system 400 may be coupled via bus 402 to a display 412, such as a cathode ray tube (CRT), for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane.

Computer system 400 may implement the techniques described herein using customized hard-wired logic, one or more ASICs or FPGAs, firmware and/or program logic which in combination with the computer system causes or programs computer system 400 to be a special-purpose machine. According to one embodiment, the techniques herein are performed by computer system 400 in response to processor 404 executing one or more sequences of one or more instructions contained in main memory 406. Such instructions may be read into main memory 406 from another storage medium, such as storage device 410. Execution of the sequences of instructions contained in main memory 406 causes processor 404 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 410. Volatile media includes dynamic memory, such as main memory 406. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 402. Transmission media can also take the form of acoustic or light waves, such as those generated during radio-wave and infrared data communications.

Various forms of media may be involved in carrying one or more sequences of one or more instructions to processor 404 for execution. For example, the instructions may initially be carried on a magnetic disk or solid-state drive of a remote computer. The remote computer can load the instructions into its dynamic memory and send the instructions over a telephone line using a modem. A modem local to computer system 400 can receive the data on the telephone line and use an infra-red transmitter to convert the data to an infra-red signal. An infra-red detector can receive the data carried in the infrared signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card, cable modem, satellite modem, or a modem to provide a data communication connection to a corresponding type of telephone line. As another example, communication interface 418 may be a local area network (LAN) card to provide a data communication connection to a compatible LAN. Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the world wide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 428, ISP 426, local network 422 and communication interface 418.

The received code may be executed by processor 404 as it is received, and/or stored in storage device 410, or other non-volatile storage for later execution.

3. Mobile Soil Analysis System
3.1 System Overview

Figure 7:
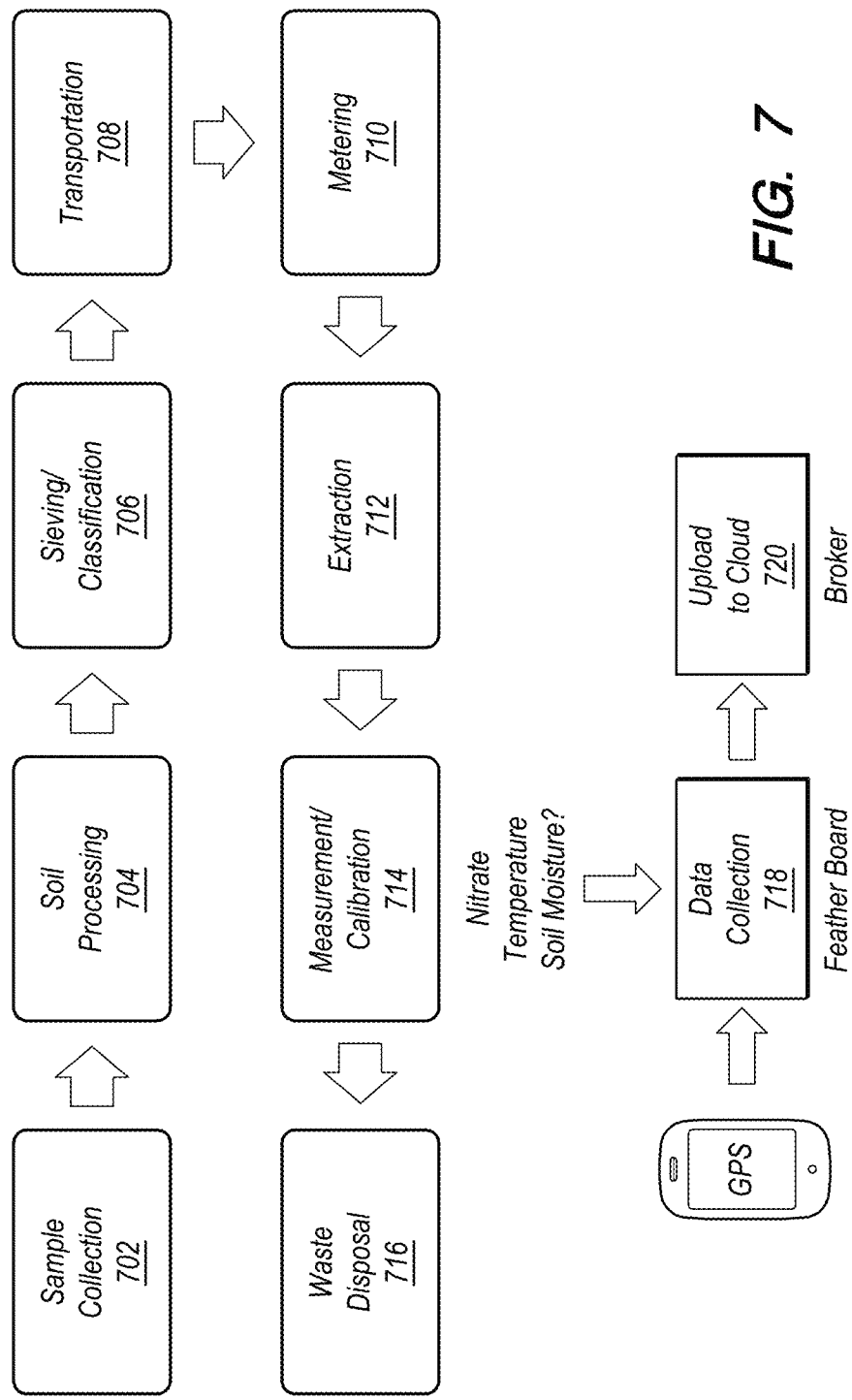
FIG. 7 illustrates an example process of collecting and analyzing soil samples in a field performed by a mobile soil analysis system.

FIG. 7 illustrates an example process of collecting and analyzing soil samples in a field performed by a mobile soil analysis system. In some embodiments, the mobile soil analysis system can travel through a field, repeatedly collecting a soil sample along the way and measuring soil element concentration in real time. The mobile soil analysis system can comprise an apparatus that is capable of processing an accumulation of multiple soil samples and measuring the concentration level of a particular soil element in each of the multiple soil samples in real time. Thus, the mobile soil analysis system can use this apparatus to process up to a certain number of successively collected soil samples and replace or refresh the apparatus from time to time, as it travels through the field.

In some embodiments, the mobile soil analysis system is configured to collect soil samples at predetermined locations or times, such as following a predetermined route and making collections periodically. The mobile soil analysis system can travel at different speeds at different times, such as faster between sample collection points but slower around sample collection points. The mobile soil analysis system can maintain an average speed between 1 and 12 miles per hour, and collect a soil sample every 10-60 feet, for instance.

In some embodiments, for each soil sample, the mobile soil analysis system is configured to perform one or more of the following steps: sample collection 702, soil processing 704, sieving or classification 706, transportation 708, metering 710, extraction 712, measurement or calibration 714, and waste disposal 716. These steps can be performed in the indicated order or in another order. The mobile soil analysis system can be configured to additionally perform data collection 718 or upload to cloud 720. The additional steps can also be performed by the server or a user computer, as noted previously.

In some embodiments, in sample collection 702, the mobile soil analysis system is configured to collect a soil sample of a specific size at a particular depth of the field through a soil probe. The soil probe can be a cutting wheel, cutting disk/plow, a bucket wheel, or a core/camshaft, for instance. A cutting/disk plow apparatus may comprise a cutting wheel to break up soil, a scoop to guide soil into an elevator or auger or screw to transport soil upward. Other types of soil probes known to someone skilled in the art can be used. The soil probe can collect and otherwise process a soil sample as the mobile soil analysis systems is moving, although it may require a decrease of the moving speed. The soil sample size can have a range of 60 plus or minus 12 grams, and the sampling depth can have a range between 0 and 12 inches.

In some embodiments, in soil processing 704, the mobile soil analysis system is configured to break down the soil in a soil sample and produce ground, relatively homogeneous soil through a soil grinder. The soil grinder can be a roller mill or a rotating blade. Other types of soil grinders known to someone skilled in the art can be used.

In some embodiments, in sieving or classification 706, the mobile soil analysis system is configured to retain primary soil particles and exclude undesirable soil aggregates that may not be conducive to downstream analysis through a soil sieve. The soil sieve can be made of stainless steel having a 2-mm diameter. Other types of soil sieves known to someone skilled in the art can be used.

In some embodiments, in transportation 708, the mobile soil analysis system is configured to transport a soil sample through a soil transporter, such as from a soil probe, a soil grinder, or a soil sieve to a soil metering component or a soil element extractor, as further discussed below. The soil transporter can be an auger screw or a bucket elevator. Other types of soil transporters known to someone skilled in the art can be used.

In some embodiments, in metering 710, the mobile soil analysis system is configured to measure various properties of a soil sample, such as its volume, weight, density, or moisture content through a soil meter. The soil meter can be a volumetric water content sensor, a weight bucket, a bulk weight measuring apparatus, or an in-line microwave. Other types of soil meters known to someone skilled in the art can be used.

In some embodiments, in extraction 712, the mobile soil analysis system is configured to extract a target soil element from a soil sample through an extraction apparatus. In measurement or calibration 714, the mobile soil analysis system is configured to detect the amount of a target soil element in the extraction apparatus through a chemical sensor. The mobile soil analysis system is further configured to analyze the data produced by the chemical sensor to determine the concentration level of the target soil element in each of soil samples provided to the extraction apparatus through a processor. In waste disposal 716, the mobile soil analysis system is configured to dispose of waste material that might have been produced in extraction, measurement or calibration, or another step. The extraction apparatus, the chemical sensor, the processor, and the waste disposal will be discussed in detail in the next section.

In some embodiments, the mobile soil analysis system is configured to detect the current location through a location sensor, such as a GPS. The mobile soil analysis system can be further configured to transmit the data produced by the location sensor, the chemical sensor, the soil meter, or the processor to the server in data collection 718 or upload to cloud 720, where the cloud may include the model data field data repository 160 in FIG. 1.

Figure 8:
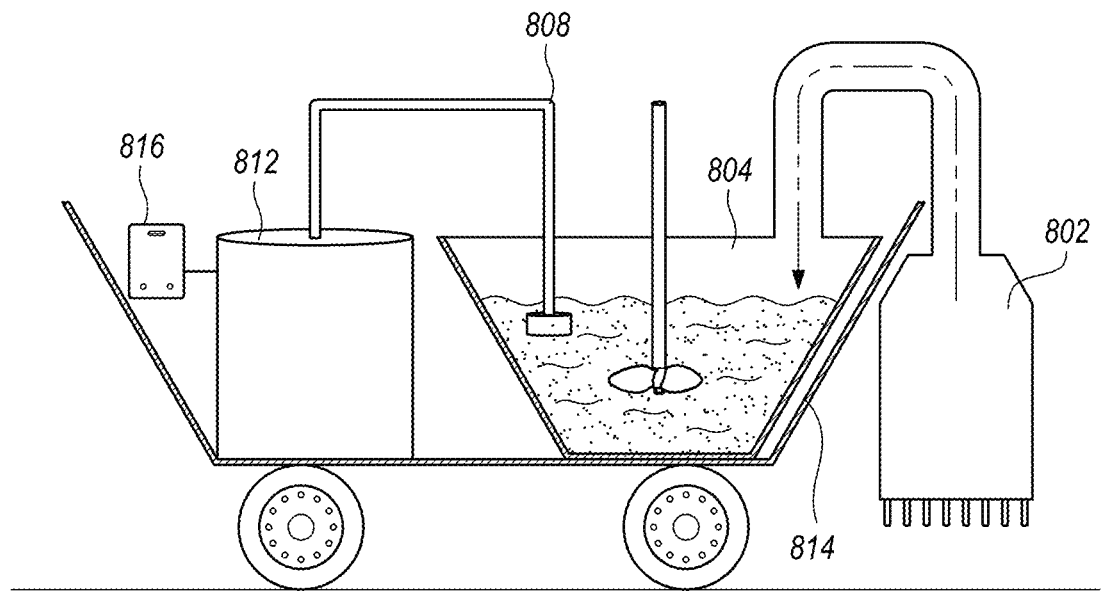
FIG. 8 illustrates an example mobile soil analysis system.

FIG. 8 illustrates an example mobile soil analysis system. In some embodiments, the mobile soil analysis system 800 can comprise a mobility component 814 for providing mobility. The mobility component 814 can be a vehicle that is capable of moving while carrying one or more other components of the mobile soil analysis system 800. The vehicle can travel on the ground, such as a planter or an all-terrain vehicle ("ATV"), or in the air, such as an UAV. The vehicle can be operated via a motor, mechanically, or manually.

In some embodiments, the mobile soil analysis system 800 can comprise a soil probe 802 for collecting a soil sample from a field and an extraction apparatus 804 for extracting a target soil element from a soil sample. The soil probe 802 can be directly coupled to the mobility component 814 and include a soil transporter for transporting the soil sample to another component of the mobile soil analysis system 800, such as the extraction apparatus 804. The soil transporter can also be separate component connecting two or more components of the mobile soil analysis system 800, such as the soil probe 802 and the extraction apparatus 804. A soil grinder for breaking down the soil in a soil sample, a soil sieve for selecting desirable soil particles from a soil sample, or a soil meter for measuring a property of a soil sample can also be incorporated into the mobile soil analysis system 800 along the path from the soil probe 802 to the extraction apparatus 804.

An example of how a soil sample is prepared for the extraction apparatus 804 is described as follows. During collection of a soil sample, a hydraulic-powered soil probe 802 can be lowered into the soil by a carrying frame as part of a soil transporter. While moving over a defined travel distance, the soil probe 802 can cut a soil core at a certain depth and the soil transporter can transport a portion of chopped soil produced by the soil probe 802 onto an intermediary pocket soil sample holder, which can also be part of a soil meter positioned above the extraction apparatus 804. The soil probe 802 can have integrated a soil grinder and a soil sieve to produce a soil sample of uniform bulk density and finely granulated particles, which facilitates a subsequent nitrate extraction process. The soil sample can then be subject to a scraper placed above the pocket sample holder, which can move to remove excess soil before the soil sample is added into the extraction apparatus 804.

In some embodiments, the mobile soil analysis system 800 can comprise a chemical sensor 808 for detecting the amount of a target soil element in the extraction apparatus 804, a processor 812 for analyzing data produced by the chemical sensor 808, and a location sensor 816 for detecting the current location. The chemical sensor 808 can be coupled to the extraction apparatus 804, and the processor 812 can in turn be coupled to the chemical sensor 808. The location sensor 816 can also be coupled to the processor 812. One or more of the chemical sensor 808, the processor 812, and the location sensor 816 can be directly coupled to the mobility component 814. A waste disposal mechanism for disposing of waste material generated by the extraction apparatus 804 or another component can also be incorporated into the mobile soil analysis system 800. The extraction apparatus 804, the chemical sensor 808, the processor 812, and the waste disposal will be discussed in detail in the next section.

3.2 Real-Time Soil Extraction, Sensing, and Measurement Unit

Figure 9:
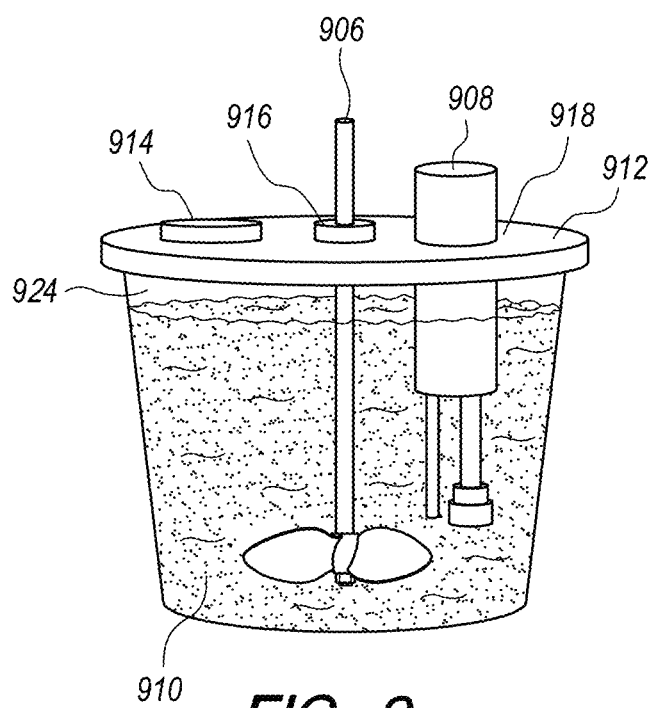
FIG. 9 illustrates an example extraction apparatus and chemical sensor.

FIG. 9 illustrates an example extraction apparatus and chemical sensor. In an embodiment, the extraction apparatus may be implemented using a removable assembly, which alone or in combination with a chemical sensor may be termed a cartridge, that may fit into and be removed from the mobile soil analysis system 800 of FIG. 8. Using a removable, replaceable cartridge, soil can be collected using the mobile soil analysis system 800 at several successive, different points in a field, with a set of multiple soil samples from multiple points placed into a cartridge that is removed before the next set of multiple samples is to be collected. The removable, replaceable property permits the mobile soil analysis system 800 to operate as an on-the-go soil sampling system capable of taking multiple successive in-field samples while travelling using modular, convenient components that reduce the amount of time and increase efficiency of obtaining samples across a distributed field area.

In some embodiments, the extraction apparatus comprises a container 924 for holding an extractant solution 910 and multiple soil samples. The extractant solution 910 is capable of dissolving the target analyte in the soil, such as nitrate. The extraction apparatus can have certain openings for receiving soil samples and other components of the mobile soil analysis system 800. For example, the extraction apparatus can include a lid 912 with one or more openings. A first opening 914 can be for receiving a soil sample. A second opening 916 can be for inserting a mixer 906 configured to mix the soil sample into the extractant solution that may already have one or more soil samples mixed in (the "solution mix" hereinafter). The second opening 916 can be a mere junction point instead when the mixer 906 is integrated into the extraction apparatus. A third opening 918 can be for inserting a chemical sensor 908 configured to detect the amount of the target analyte in the solution mix. The mixer 906 or the chemical sensor 908 can be coupled to the lid 912, to the container 924, or another portion of the mobility soil analysis system using common fastening means, such as soldering, screws, or adhesives. The lid 912 can fit the container 924 and stay in place when the container 924 is being replaced.

In some embodiments, the container 924 can be a self-contained disposable unit or a static solution tank. The container 924 can be made of a material that can endure through field trips and that does not react with the solution mix, such as plastic. The container can have a round base to facilitate the movement of solution mix during mixing. A self-contained disposal unit can be moved aside and eventually carried away from the mobile soil analysis system 800 as part of the waste disposal. The self-contained disposable unit can be replaced by another one when the solution mix has reached saturation, when a certain number of soil samples have been added to the extractant solution 910 or solution mix, when a certain amount of time has elapsed, or when another condition is satisfied. A static solution tank stays in place but its content undergoes processing cycles, each starting with an extractant solution 910 that may need to be poured in, comprising the extractant solution 910 or solution mix being combined with more soil samples over time, and ending with the solution mix purified for reuse or drained as part of the waste disposal.

In some embodiments, the extractant solution 910 can contain water or a dilute salt solution, for example, because essentially all the nitrate in the soil with low anion exchange capacities is water soluble. Depending on the type of the chemical sensor 908, certain cautionary measures can be taken with the extractant solution 910. For example, when nitrate as nitrogen NO3-N is measured by ion chromatography or ion selective electrode ("ISE"), chloride in the extractant solution 910 can interfere with the analysis. In this case, ammonium sulfate $(NH_4)_2SO_4$ can be a preferred extractant, for instance. Alternatively, selective inhibitor chelators can be added to a non-specific extractant solution

910 to eliminate interference with the target analyte. Some chelators, such as the Nitrate Interference Suppressor Solution ("NISS"), are commercially available and can be added into the extractant solution 910 for the use of ISE nitrate sensors. Use of the NISS frees the ISE from most interferences present in soils (i.e., anions such as chloride). Other candidate sensors, such as a SupraSensor, does not generally require NISS in the extractant solution 910 since anions do not interfere with the nitrate sensing of the SupraSensor. In addition, as the minimal detection limit of an ISE for nitrate is about 1.4 ppm, a baseline of 2-5 ppm of nitrate can be added to the extractant solution 910 to avoid low level measurements in the non-linear region of the ISE. Specifically, pure nitrate can be added in water at this baseline concentration, and the combination can be added into the extractant solution 910.

In some embodiments, the mixer 906 can be an overhead stirrer that can be inserted downward into the container 924 through the opening 916 in the lid 912 and can comprise paddles or blades on the bottom for stirring. The size of the paddles or blades can depend on the size of the container 924, the volume of the solution mix, the desired stirring speed, or other factors. The overhead stirrer can be made of a material that would not be deformed from stirring impact and would not interact with the solution mix, such as steel. The overhead stirrer can be coupled to a motor that is coupled to the mobility soil analysis system for automated stirring with a speed of at least 10 rpm, to allow the nitrate dissolution or extraction to complete and the solution mix ready for measurement within one second. The mixer 906 can also be a recirculating pump that constantly stirs the solution mix through air pressure. The recirculating pump can be configured to have a mixing speed above 10 rpm, to allow the dissolution or extraction to complete within one second.

In some embodiments, the chemical sensor 908 can comprise an ISE, which is capable of direct moist soil sensing. For example, a nitrate ISE can be used to measure the concentration of nitrate NO3- in aqueous samples. The ISE can be a traditional ISE based on liquid junction or a modern solid-state ISE based on solid junction. Generally, an ISE converts the activity of a specific ion dissolved in a solution into an electrical potential. A commercial ISE can include a processing unit that further converts the electrical potential measured for the target analyte into a human-readable concentration level. Such a commercial ISE can have a range of at least 0.1-14,000 ppm, while the expected range of a target soil element can be 0-50 ppm, for example. Furthermore, such a commercial ISE is expected to produce a reading within 10 seconds with a reproducibility of being within plus or minus 10% of a full scale. Prior to use, the ISE can be calibrated using prepared reagent-grade target analyte standards solutions, to ensure that the sensors are operating as expected. For example, sensors can be inserted into pure nitrate standard solutions (e.g., 10 and 100 ppm nitrate in water), a slope can be determined, and then the nitrate response can be calculated to a defined test sample using a linear equation based on the slope. The ISE may need to be replaced from time to time as part of the waste disposal. Other types of sensors can be used, such as a SupraSensor built using a microchip-based technology with proprietary chemical coating (ChemFET) that selects specifically for nitrate.

In some embodiments, the size of the container 924 and the amount of the extractant solution 910 can depend on the amount of soil to be dissolved, the amount of target analyte present in the soil, the sensitivity of the chemical sensor 908, or other factors. The amount of soil to be dissolved is in turn related to the frequency of soil sample collection and the size of a collected soil sample. As discussed above, in one desirable scenario, the mobile soil analysis system 800 can move at an average speed of roughly 12 miles per hour and collect a soil sample roughly every 10 feet, which means that a soil sample would be collected as frequently as every 6-10 seconds. Such a frequency can impose constraints on the mixing speed of the mixer 906 and the detection speed of the chemical sensor 908, as further discussed below. Further in the desirable scenario, each soil sample collected can weigh roughly 60 grams. Based on a maximum of 20 soil samples to be dissolved in the extractant solution 910 and an extractant to soil weight ratio of 10:1, the amount of the extractant solution 910 can be calculated. Based on the densities of the soil and the extractant solution 910, the amount of space needed for the mixing to be effective, or other factors, the size of the container 924 can then be estimated. The size of the container 924 may also be limited by the capacity of the mobility component in the soil analysis system, the capability of the waste proposal, or other factors. A maximum of 20 soil samples would also require that the container 924 be purified or replaced roughly every 2-3 minutes. The container volume can be further customized to satisfy specific throughput or other requirements. For example, the container volume can be increased to lower the replacement rate.

In some embodiments, the processor 812, can be coupled with the chemical sensor 808 or specifically the chemical sensor 908 and receive data from the chemical sensor 808 for further processing, as discussed above. FIG. 10 illustrates converting data showing cumulative concentration levels in a solution mix to concentration levels in individual soil samples. FIG. 10A illustrates an example diagram showing how the nitrate concentration level in the solution mix changed as 20 soil samples were successively mixed into the extractant solution, as measured by the chemical sensor. FIG. 10A comprises a line graph in which the vertical Y axis indicates nitrate concentration in parts per million (PPM) and the horizontal X axis indicates time in seconds. In the example graph of FIG. 10A, a soil sample is added roughly every 100 seconds in this experiment. In other embodiments or experiments, the collection of a soil sample, the mixing of the soil sample into the extractant solution, and the measurement of the concentration level of the target analyte in the solution mix is expected to be completed within 6-10 seconds, as noted above. Each nearly vertical segment in the curve indicating a fast increase in the nitrate concentration level essentially corresponds to an addition of a soil sample into the extractant solution or solution mix.

FIG. 10B illustrates an example diagram showing the nitrate concentration level in each of the 20 soil samples successively added to the solution mix, as computed by the processor 812. FIG. 10B comprises a bar chart in which the vertical Y axis specifies nitrate concentration calculated as PPM and the horizontal X axis specifies a particular sample from among a plurality of samples, such as up to 20 samples in this example. The processor 812 may be programmed to take the data shown in FIG. 10A and determine the amount of each fast increase to produce the data shown in FIG. 10B. For example, each increase of more than a first quantity threshold that occurs within a second duration threshold can be identified. While this figure shows that the nitrate concentration level in each soil sample can be as high as roughly 100 ppm in this experiment, in other embodiments or experiments the nitrate concentration level is expected to be between 0-50 ppm and the chemical sensor is expected to be sufficiently sensitive to detect the relatively low concentration levels.

FIG. 10C illustrates sample statistics related to the experiment. FIG. 10C is a data table that identifies nitrate concentration, soil NO3 as measured in a laboratory, average NO3 as measured using a cartridge such as that illustrated in FIG. 8 or FIG. 9, a standard deviation, percentage recovery, precision, and accuracy, with example values for each specified metric. In the example of FIG. 10C, the percentage recovery was approximately 95 and the accuracy or percentage of relative error was approximately −5.3. Here, the percent of recovery refers to the amount of nitrate measured by the sensor out of the total amount initially present in the soil sample under the test conditions; the amount not in solution would become unrecovered nitrate. In addition, the percent of relative error (a negative value) generally estimates the accuracy of an assay and in this case specifically refers to the amount of nitrate not measured out of the expected 100% in the soil. These statistics are expected to remain similar if not unchanged in a production setting noted above.

In some embodiments, the processor 812 is configured to perform further analysis and generate recommendations for users. The processor can also receive additional data from a location sensor, as discussed above, and create a nitrate map for the field indicating the nitrate concentration level for each unit of the field. The processor can also receive additional data indicating various factors affecting the health of the field, such as weather reports, fertilization histories, target yield amounts, moisture indicators, or pollutant updates, and generate actionable recommendations. For example, by determining how effective certain fertilizers can be in general and how much nutrient is currently in one area of the field, the processor can suggest how much fertilizer to apply to the area to achieve a certain crop yield. The processor can then transmit the recommendations to a central server or to a user computer.

In some embodiments, the processor can be coupled with the mobility component of the mobile soil analysis system 800 as noted above and configured to perform computations as the mobile soil analysis system 800 travels in the field. The processor can be connected to the chemical sensor physically or wirelessly when the chemical sensor includes an integrated networking component. The processor can also be integrated with a controller for the mobile soil analysis system 800 that is coupled to the mobility component, as further discussed below. Alternatively, the processor can be separate from the mobile soil analysis system 800 and reside in a remote location. For example, the processor can be integrated into a central server or a user computer and communicate with the chemical sensor over a communication network.

Figure 11:
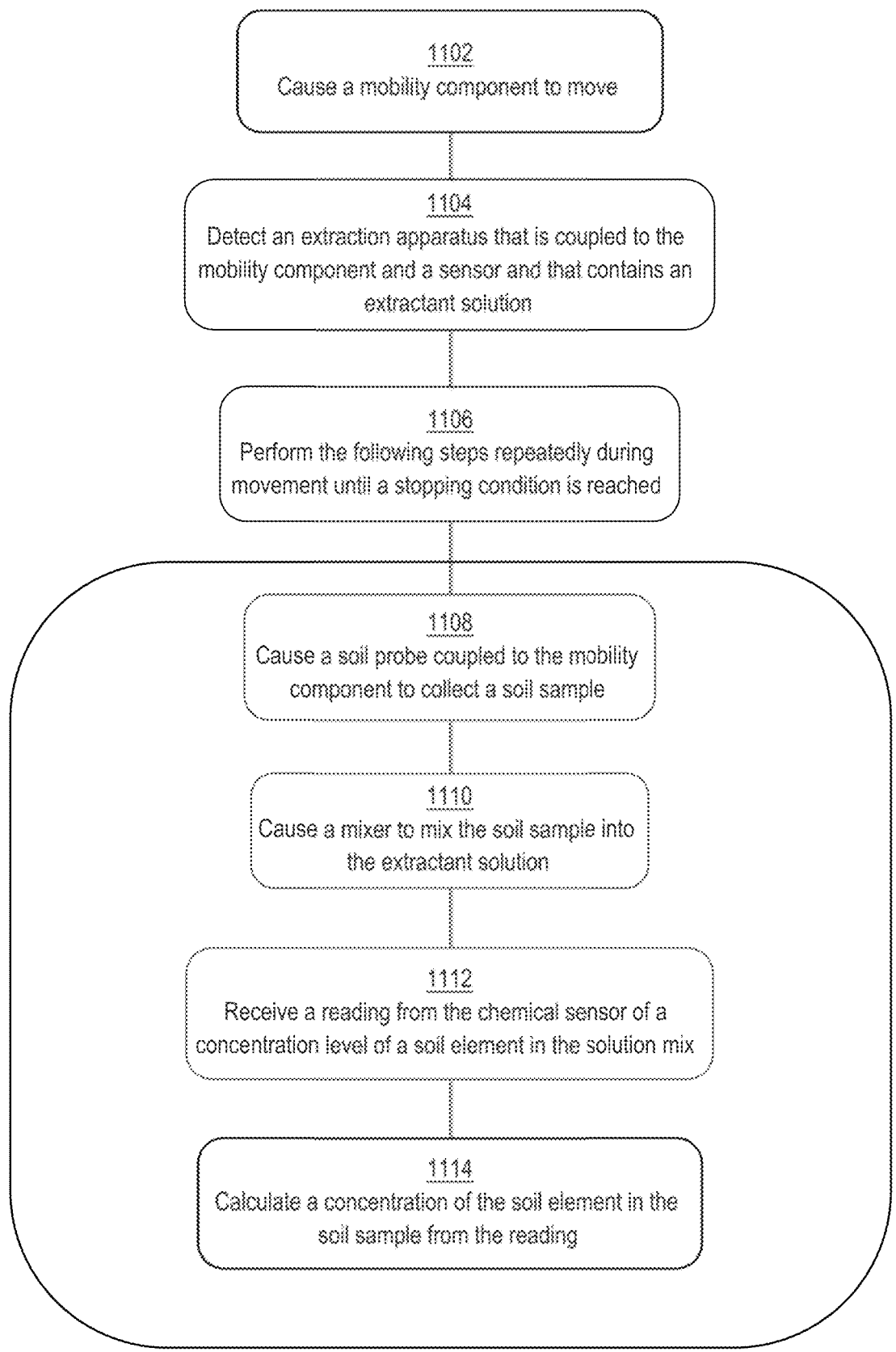
FIG. 11 illustrates an example process of controlling the mobile soil analysis system to determine soil element concentration in soil samples in real time performed by a processor, such as an application or device controller.

FIG. 11 illustrates an example process of controlling the mobile soil analysis system 800 to determine soil element concentration in soil samples in real time performed by a processor, such as an application or device controller. In some embodiments, in step 1102, the processor is configured to cause the mobility component to move. This can be in response to receiving an instruction from a remote user computer or a user action of turning on a switch within the mobile soil analysis system 800, for example. In step 1104, the processor is configured to detect an extraction apparatus and a chemical sensor. The chemical sensor may signal to the processor its own operational status as well as the operational status of the extraction apparatus, including a confirmation that a certain amount of extractant solution is ready in a container of the extraction apparatus. In step 1106, the processor is configured to perform steps 1108, 1110, 1112, and 1114 repeatedly and in real time as soil samples are successively collected. For example, these steps can be performed every 6-10 seconds.

In some embodiments, in step 1108, the processor is configured to cause a soil probe to collect a soil sample. The processor can control the depth of probing, such as 6-12 inches, the amount of soil collected, such as 60 grams, and other parameters in soil collection. The processor can be further configured to cause proper operation of a soil grinder, a soil sieve, or a soil transporter to produce a soil sample ready to be mixed into the extractant solution before the next soil sample is collected. In step 1110, the processor is configured to cause a soil mixer to mix a soil sample into the extractant solution or the solution mix. The processor can control the position or speed of the mixer or the manner of mixing to extract as much of the target soil element as possible within the shortest amount of time. In step 1112, the processor is configured to receive a reading from the chemical sensor of the cumulative concentration level of the target analyte in the solution mix. The processor could store the readings for further processing. The processor could be further configured to determine whether the cumulative concentration level is within a normal range and cause reporting of an error or a warning when the cumulative concentration level falls outside the normal range. For example, the warning may signal a cleaning or replacement of the extraction apparatus when too much soil has been added to the extractant solution, when the mixing was unsuccessful, or when the container was broken. In step 1114, the processor is then configured to calculate a concentration level of the target analyte in the soil sample just added into the solution mix. The processor can be further configured to calculate an amount of target analyte to be added to the area where the soil sample was collected and transmit a recommendation of such an amount. By virtue of these features, as the mobile soil analysis system 800 travels in the field, it can measure the amount of nitrate currently in an area of the soil and apply an appropriate amount of fertilizer to that area of the soil in real time. In addition, the processor could be configured to receive additional data from a location sensor or transmit the calculated concentration level, received location information, or recommended amount of nutrient to be added to a remote server or user computer or save it in a local memory.

What is claimed is:

1. A system for measuring soil element concentration in an agricultural field as the system moves through the agricultural field, comprising:
   a mobility component configured to move through the agricultural field;
   a soil probe coupled to the mobility component and configured to obtain a succession of soil samples from different locations as the system moves through the agricultural field;
   an extraction apparatus coupled to the mobility component configured to add the succession of soil samples into a cartridge containing an extractant solution, thereby forming a solution mix;
   a chemical sensor coupled to the extraction apparatus configured to measure a concentration level of a soil element in the solution mix;
   a processor coupled to the chemical sensor, the processor configured to calculate a concentration level of the soil element in each of the succession of soil samples after the soil sample is added into the cartridge by the extraction apparatus and before a successive soil sample is added.

2. The system of claim 1, further comprising:
a soil grinder configured to break down soil in a soil sample of the succession of soil samples;
a soil sieve configured to select desirable soil particles from the soil sample.

3. The system of claim 1, further comprising a soil scraper configured to remove excess soil from a soil sample before a resulting soil sample is added to the extraction apparatus.

4. The system of claim 1, the mobility component configured to move through the agricultural field while carrying one or more other components of the system through air.

5. The system of claim 1, further comprising a soil transporter coupled to the soil probe and configured to move a soil sample from the soil probe to another component of the system.

6. The system of claim 1, the cartridge having one or more openings for receiving a soil sample, inserting a mixer, or inserting a chemical sensor.

7. The system of claim 1,
the cartridge having a lid and a container,
the container being a self-contained disposable unit,
the lid having one or more openings and staying in place while the container is being replaced.

8. The system of claim 1,
the cartridge having a lid and a container,
the container being made of plastic and having a round base.

9. The system of claim 1, the extractant solution including ammonium sulfate and 2-5 ppm of nitrate as a baseline.

10. The system of claim 1, an amount of the extractant solution being determined based on an amount of soil to be dissolved from the succession of soil samples, an amount of soil element in the soil, or a sensitivity of the chemical sensor.

11. The system of claim 1, the extraction apparatus comprising a mixer that has a stirrer on a bottom and is made of steel.

12. The system of claim 1, the extraction apparatus comprising a mixer that is a recirculating pump that constantly stirs the solution mix through air pressure.

13. The system of claim 1,
the extraction apparatus comprising a mixer,
a target speed of the mixer being determined based on a speed at which the succession of soil samples is obtained, a volume of each soil sample of the succession of soil samples, or an amount of expectant solution.

14. The system of claim 1, the chemical sensor being built using a microchip-based technology with chemical coating (ChemFET) that selects specifically for nitrate.

15. The system of claim 1,
the processor further configured to receive additional data related to health of the agricultural field, including weather reports, fertilization histories, target yield amounts, moisture indicators, or pollutant updates,
the processor further configured to generate a recommendation for improving the agricultural field based on the calculated concentration levels and the additional data.

16. The system of claim 1,
the processor further configured to receive a known fertilizer level for a healthy agricultural field,
the processor further configured to determine a recommended fertilizer level based on the known fertilizer level and the calculated concentration level of one soil sample of the succession of soil samples.

17. A non-transitory machine-readable storage medium storing instructions that when executed by a processor, cause the processor to execute a method of measuring soil analyte concentration in a field, the method comprising:
detecting an extraction apparatus coupled to a mobility component and a chemical sensor coupled to the extraction apparatus, the extraction apparatus comprising a mixer and a container holding an extractant solution, the mobility component configured for movement through the field; and
during movement of the mobility component until a stopping condition is reached, for each of a plurality of locations reached by the mobility component, performing:
causing the extraction apparatus to receive a soil sample from the location from a soil probe coupled to the mobility component;
causing the mixer to mix the soil sample into the extractant solution forming a solution mix containing successively collected soil samples;
receiving a reading from the chemical sensor of a concentration level of a target analyte in the solution mix; and
calculating a concentration level of the target analyte in the soil sample from the reading, before a successive soil sample from a different location is received by the extraction apparatus.

18. The non-transitory machine-readable storage medium of claim 17, the method further comprising:
receiving additional data related to health of the field, including weather reports, fertilization histories, target yield amounts, moisture indicators, or pollutant updates;
generating a recommendation for improving the field based on the calculated concentration levels and the additional data.

19. The non-transitory machine-readable storage medium of claim 17, the method further comprising:
receiving a known fertilizer level for a healthy field;
determining a recommended fertilizer level based on the known fertilizer level and the calculated concentration level of one soil sample for one of the plurality of locations.

20. The non-transitory machine-readable storage medium of claim 17, the method further comprising, during movement of the mobility component, for each of a plurality of locations reached by the mobility component:
receiving a geographic coordinate of the location;
transmitting the calculated concentration level of the target analyte in the soil sample and the geographical coordinate to generate a target analyte map.

* * * * *